United States Patent
Pei et al.

(10) Patent No.: US 12,252,728 B2
(45) Date of Patent: Mar. 18, 2025

(54) SYSTEMS AND METHODS FOR MEASURING LIVER ENZYME LEVELS IN BLOOD

(71) Applicant: Nova Biomedical Corporation, Waltham, MA (US)

(72) Inventors: Jianhong Pei, Somerville, MA (US); Joseph Bedard, Waltham, MA (US); Yiliyasi Wusimanjiang, West Newton, MA (US); Anthony Florindi, Norfolk, MA (US); Chung Chang Young, Salem, NH (US)

(73) Assignee: NOVA BIOMEDICAL CORPORATION, Waltham, MA (US)

( * ) Notice: Subject to any disclaimer, the term of this patent is extended or adjusted under 35 U.S.C. 154(b) by 293 days.

(21) Appl. No.: 17/256,210

(22) PCT Filed: Sep. 17, 2019

(86) PCT No.: PCT/US2019/051383
§ 371 (c)(1),
(2) Date: Dec. 27, 2020

(87) PCT Pub. No.: WO2021/054937
PCT Pub. Date: Mar. 25, 2021

(65) Prior Publication Data
US 2021/0363560 A1    Nov. 25, 2021

(51) Int. Cl.
*C12Q 1/00* (2006.01)
*C12Q 1/42* (2006.01)
(Continued)

(52) U.S. Cl.
CPC .............. *C12Q 1/005* (2013.01); *C12Q 1/42* (2013.01); *C12Q 1/48* (2013.01); *G01N 27/3272* (2013.01); *G01N 27/48* (2013.01)

(58) Field of Classification Search
CPC . C12Q 1/005; C12Q 1/42; C12Q 1/48; G01N 27/3272; G01N 27/48
See application file for complete search history.

(56) References Cited

U.S. PATENT DOCUMENTS

| | | | |
|---|---|---|---|
| 3,932,131 A * | 1/1976 | Rolfo-Fontana | G01N 35/02 436/98 |
| 6,602,989 B1 * | 8/2003 | Sadik | G01N 33/5308 530/391.1 |

(Continued)

FOREIGN PATENT DOCUMENTS

| | | |
|---|---|---|
| KR | 20180003061 U | 10/2018 |
| WO | 0005581 A1 | 2/2000 |

(Continued)

OTHER PUBLICATIONS

European Search Report received in European Patent Application No. 19938105.4, dated Jan. 13, 2022, 7 pages.

(Continued)

*Primary Examiner* — Adam Weidner
*Assistant Examiner* — Trent R Clarke
(74) *Attorney, Agent, or Firm* — Hayes Soloway PC

(57) ABSTRACT

A disposable test cartridge to determine the concentration of one or more liver enzymes in a blood sample includes a cartridge body having a plurality of chambers where at least one of the chambers contains a reactant mixture that reacts when catalyzed by one of the liver enzymes ALT, AST, ALP, or GGT in a blood sample forming a reaction solution, a removable cartridge cover connected to the cartridge body, and a test strip module connected to the cartridge body. The test strip module containing at least one analyte test strip configured for receiving a portion of the reaction solution and electrochemically measuring at least one analyte that is a reaction product in the reaction solution.

31 Claims, 13 Drawing Sheets

(51) Int. Cl.
*C12Q 1/48* (2006.01)
*G01N 27/327* (2006.01)
*G01N 27/48* (2006.01)

(56) References Cited

U.S. PATENT DOCUMENTS

| | | | |
|---|---|---|---|
| 2005/0124024 A1* | 6/2005 | Woerner | C12Q 1/42 558/71 |
| 2005/0136541 A1 | 6/2005 | De Haan | |
| 2010/0036220 A1 | 2/2010 | Feldman et al. | |
| 2013/0084630 A1 | 4/2013 | Rolland et al. | |
| 2014/0072959 A1 | 3/2014 | Determan et al. | |
| 2016/0324506 A1 | 11/2016 | Tariyal et al. | |
| 2017/0183711 A1 | 6/2017 | Hughes et al. | |
| 2019/0038196 A1 | 2/2019 | Young et al. | |

FOREIGN PATENT DOCUMENTS

| | | |
|---|---|---|
| WO | 2013025899 A1 | 2/2013 |
| WO | 2021054937 A1 | 3/2021 |

OTHER PUBLICATIONS

PCT Search Report for PCT/US2019/051383 mail date Jun. 16, 2020.

PCT Written Opinion for PCT/US2019/051383 mail date Jun. 16, 2020.

Chang, Ku-Shang et al., "Sequential measurement of aminotransferase activities by amperometric biosensor", Biosensors and Bioelectronics, vol. 22 (2007), pp. 2914-2920.

Song, Min-Jung et al., "An Electrochemical Biosensor Array for Rapid Detection of Alanine Aminotransferase and Aspartate Aminotransferase," Bioscience, Biotechnology, and Biochemistry, vol. 73 (3), (2009), pp. 474-478.

Ohgami, Naoto et al., "Determination of the activities of glutamic oxaloacetic transaminase and glutamic pyruvic transaminase in a microfluidic system," Biosensors and Bioelectronics, vol. 22 (2007), pp. 1330-1336.

Guo, Zonghui et al., "The Study of a Disposable Reagentless Biosensor for Fast Test of Aspartate Aminotransferase," Electroanalysis, vol. 20 (2008), No. 10, pp. 1135-1141.

Chang, Ku-Shang et al., Effect of L-Aspatate Concentration on the Response of the Amperometric L-Glutamate Sensor for the Measurement of L-Glutamate and Aspartate Aminotransferase Activity in Serum, Analytical Letters, vol. 40 (2007), pp. 933-945.

Xuan, Guang Shan et al., "Development of an electrochemical immunosensor for analine aminotrasnferase," Biosensor & Bioelectronics, Vo. 19 (2003), pp. 365-371.

Huang, Xing-Jiu et al., "Aspartate Aminotransferase (AST/GOT) and Alanine Aminotransferase (ALT/GPT) Detection Techniques," Sensors, vol. 6 (2006), pp. 756-782.

Thuy, Tran Nguyen Thanh et al., "A Micro-Platinum Wire Biosensor for Fast and Selective Detection of Alanine Aminotransferase," Sensors, vol. 16 (2016), p. 767-ff.

Jamal, Mamun et al., "A stable and selective electrochemical biosensor for the liver enzyme alanine aminotransferase," Biosensors and Bioelectronics, vol. 24 (2009), pp. 2926-2930.

Ia Cour, Jakob B et al., "Low-cost disposable ALT electrochemical microsensors for inv-vitro hepatotoxic assessment," Sensors and Actuators B: Chemical, vol. 228 (2016), pp. 360-365.

Akbas et al., "Assessment of liver function tests on Piccolo Xpress point of care chemistry analyzer in a pediatric hospital", Elsevier, Practical Laboratory Medicine, vol. 3, 2015, pp. 1-7, 7 pages.

* cited by examiner

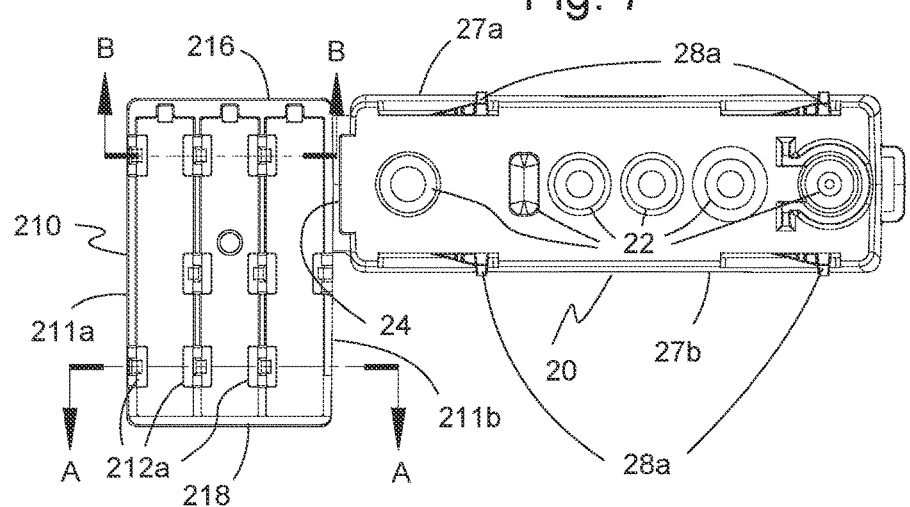
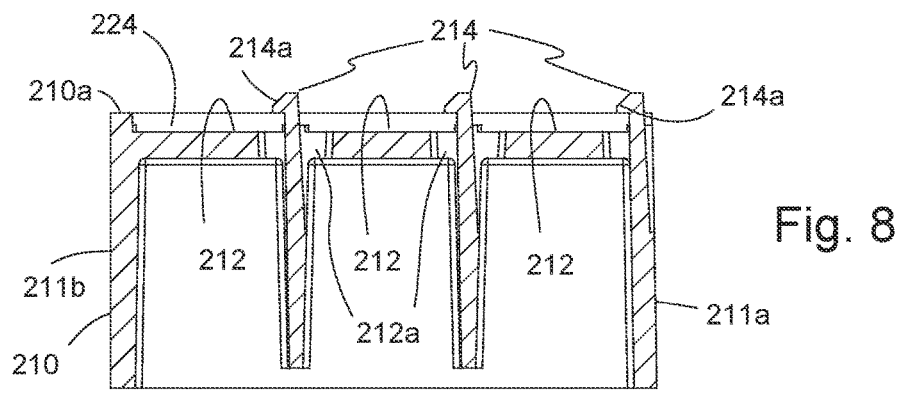
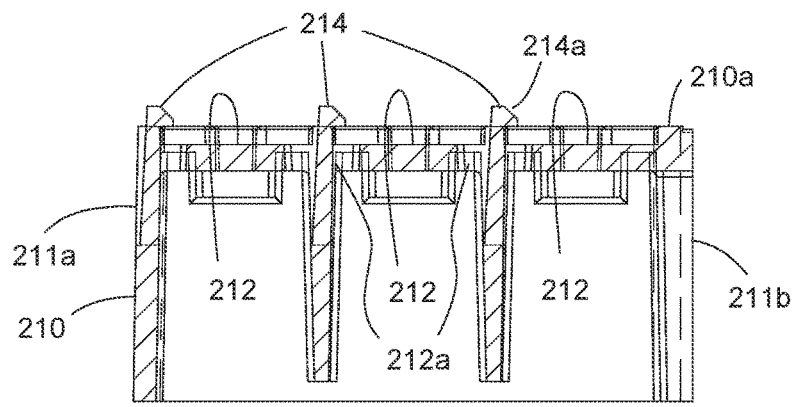

Fig. 10
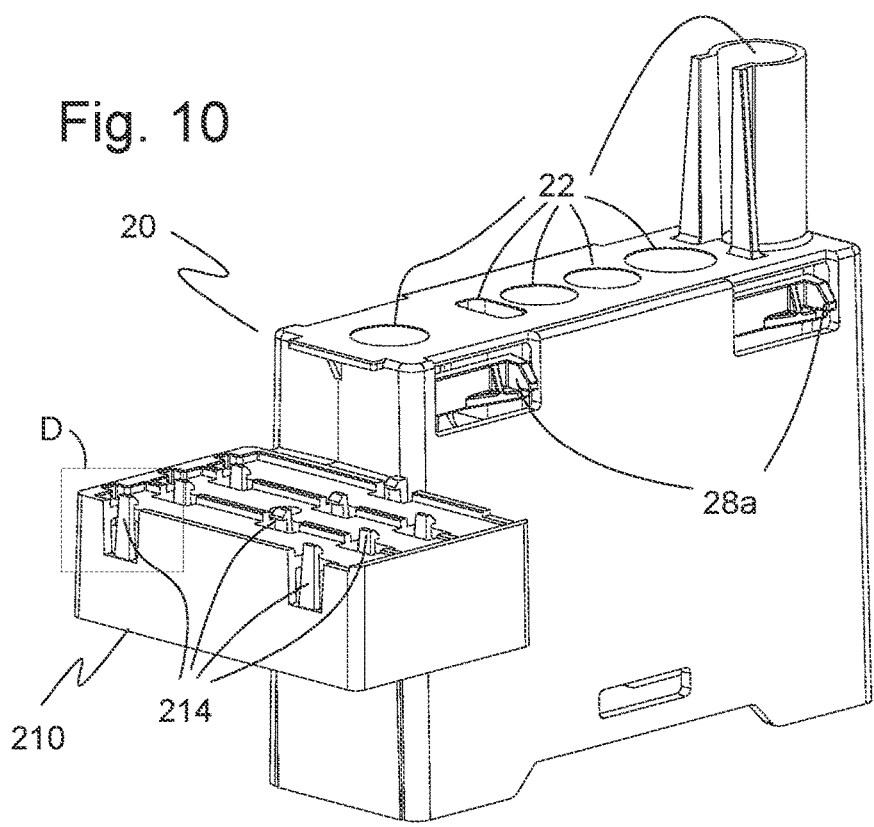
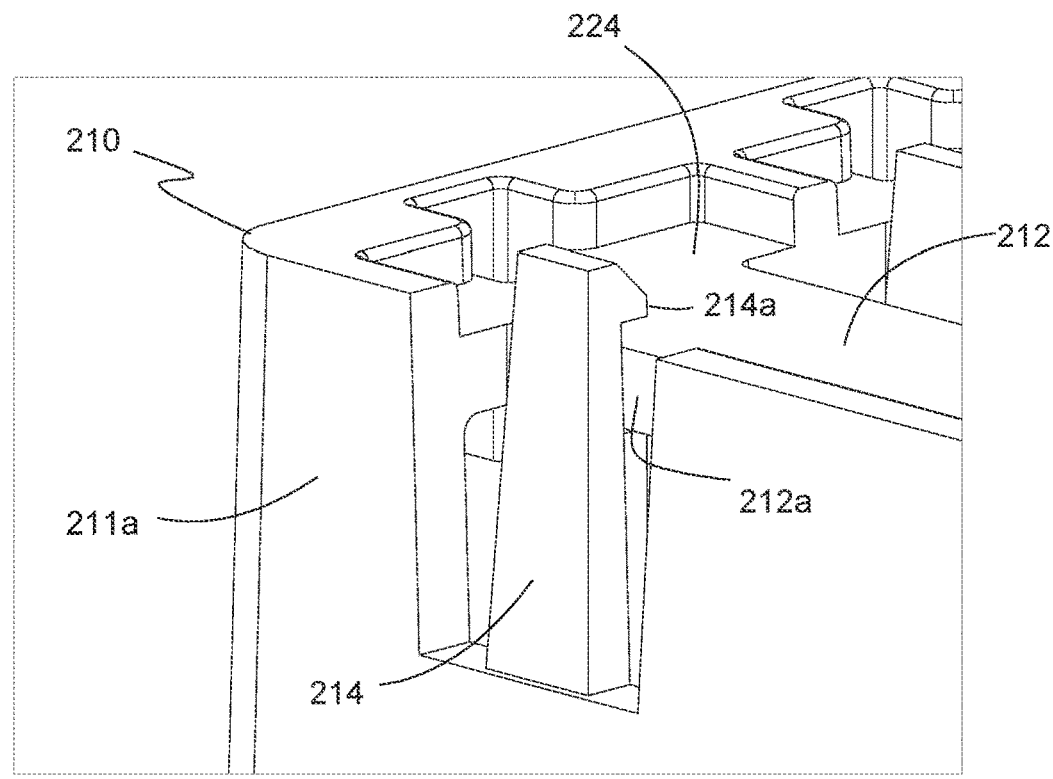
Fig. 11

SYSTEMS AND METHODS FOR MEASURING LIVER ENZYME LEVELS IN BLOOD

BACKGROUND OF THE INVENTION

1. Field of the Invention

The present invention relates generally to detection techniques for measuring enzymes activities. Particularly, the present invention relates to detection techniques for measuring liver enzyme activities.

2. Description of the Prior Art

Aminotransferases are enzymes that the liver uses to make glycogen. Glycogen is the stored form of glucose. Any glucose not immediately used will be converted into glycogen and stored in cells for future use. Most will be stored in the liver while the remainder will be stored in skeletal muscles, glial cells of the brain and other organs.

Liver enzymes are substances typically found in higher concentrations in the liver. Some of the more important liver enzymes include alanine aminotransferase (ALT), aspartate aminotransferase (AST), gamma-glutamyl transferase (GGT), and alkaline phosphatase (ALP). Any elevation in one of these liver enzyme levels found in the blood may be a sign of a liver problem.

Alanine aminotransferase (ALT) and aspartate aminotransferase (AST) are two important enzymes in the investigation for signs of a liver problem. When both are used, a comparison of ALT and AST levels are helpful to identify liver toxicity, liver disease, or liver damage.

ALT and AST are enzymes found mainly in the liver, however, they are also found in red blood cells, in heart cells, in muscle tissue, and other organs such as the pancreas and kidneys. Specifically, AST is found in a variety of tissues including the liver, brain, pancreas, heart, kidneys, lungs, and skeletal muscles. If any of these tissues are damaged, AST will be released into the blood stream. While increased AST levels are indicative of a tissue injury, it is not specific to the liver. On the other hand, ALT is found primarily in the liver. Any elevation of the ALT is a direct indication of a liver injury.

ALP is an enzyme in a person's blood that helps break down proteins. The body uses ALP for a wide range of processes, and it plays a particularly important role in liver function and bone development. Using an ALP test, it is possible to measure how much of this enzyme is circulating in a person's blood. Slightly irregular ALP levels are usually no cause for concern. Severely abnormal levels can signify a severe underlying medical condition, typically one relating to the liver, bones, or gallbladder. Since ALP is most abundant in the bones and liver, elevated ALP levels in the blood are generally a sign of a liver or bone condition. An obstruction of the liver or damage to it will cause ALP levels to rise. This will also occur if there is an increase in bone cell activity.

Abnormal ALP levels usually indicate one of the following conditions: gallstones, cholecystitis (i.e. inflammation of the gallbladder), liver cancer, abnormal and noncancerous growths on the liver, cirrhosis (i.e scarring of the liver), hepatitis (i.e. inflammation of the liver often due to infection), bile cancers, overuse of medications harmful to the liver, excessive consumption of alcohol, malnutrition (especially deficiencies in vitamin D, calcium, protein, magnesium, and zinc), and bone cancers.

GGT is an enzyme that is found in many organs throughout the body, with the highest concentrations found in the liver. Normally, GGT is present in low levels in the blood. GGT is usually the first liver enzyme to rise in the blood when any of the bile ducts that carry bile from the liver to the intestines become obstructed, for example, by tumors or stones. This makes it the most sensitive liver enzyme test for detecting bile duct problems. The GGT test, however, is not very specific and is not useful in differentiating between various causes of liver damage because it can be elevated with many types of liver diseases, such as liver cancer and viral hepatitis, as well as other non-hepatic conditions, such as acute coronary syndrome. The GGT test is not recommended for routine use by itself. However, it can be useful in conjunction with other tests and in determining the cause of a high ALP level. Both GGT and ALP are increased in liver diseases, but only ALP will be increased with diseases affecting bone tissue. Therefore, GGT can be used as a follow up to an elevated ALP to help determine if the high ALP result is due to liver or bone disease. If the GGT test results in a normal GGT level, then it likely indicates a bone issue. On the other hand, a high GGT level may signal a problem with the liver or bile ducts. GGT levels are sometimes increased with consumption of even small amounts of alcohol. Higher levels are found more commonly in chronic heavy drinkers than in people who consume less than 2 to 3 drinks per day or who only drink heavily on occasion (binge drinkers). The GGT test may be used in evaluating someone for acute or chronic alcohol abuse.

The current method of testing for ALT, AST, ALP, and GGT requires a blood sample. A blood sample is obtained by a phlebotomist or a nurse from a vein in the inner elbow of the patient using a needle and a plastic tube that is attached to the end of the needle to draw a quantity of blood. The blood sample is then sent to a clinical laboratory for analysis.

Normal lab values are measured in international units per liter (IU/L) and vary based on a person's body mass index as well as the individual lab's reference value. Typically, the normal reference range for adults is 8 to 48 IU/L for AST, 7 to 55 IU/L for ALT, 20 to 140 IU/L for ALP, and 0 to 30 IU/L for GGT. The high end of the range is used to establish how elevated the liver enzymes are. AST or ALT levels are a valuable aid primarily in the diagnosis of liver disease. The AST/ALT ratio can provide valuable clues as to what is going on and whether the issue is acute or chronic. The AST/ALT ratio is a calculation that compares the levels of AST and ALT in the blood. Depending on which value is elevated and the extent of that elevation is a strong indication as to what disease is involved.

For example, an AST/ALT ratio of less than one is suggestive of non-alcoholic fatty liver disease. An AST/ALT ratio equal to one is suggestive of acute viral hepatitis or drug-related liver toxicity. An AST/ALT ratio higher that one is suggestive of cirrhosis. An AST/ALT ratio higher than 2 to 1 is suggestive of alcoholic liver disease. The ratio alone is not sufficient. The magnitude of elevation is important.

For example, the AST would generally be more than eight times the normal upper limit and the ALT more than five times the normal upper limit in alcoholic fatty liver disease. If the AST and ALT are both more than four times the respective normal upper limit, this would be indicative of non-alcoholic fatty liver disease. In acute viral hepatitis, both the AST and the ALT would each be twenty-five times the respective normal upper limit. With chronic hepatitis C, the AST and ALT could be from two to ten time the respective normal upper limit. If the AST and ALT are over 50 times their respective normal upper limit, this is indicative of ischemic hepatopathy.

There are several detection technologies available for measuring AST and ALT, which are described in a journal article titled "Aspartate Aminotransferase (AST/GOT) and Alanine Aminotransferase (ALT/GPT) Detection Techniques," Sensors, 2006, 6, pp. 756-782. These include colorimetric analysis, spectrophotometric analysis, chemiluminescence, chromatography, fluorescence and UV absorbance, radiochemical analysis, and electrochemical techniques.

The limitations of colorimetric analysis are that it requires making calibration curves and stopping the enzyme reaction. Spectrophotometric analysis requires extra instrumentation like a spectrophotometer, 3-T Sigma scanner, and the like and, thus, are not suitable for point-of-care applications or home-use test systems. In addition, spectrophotometric methods do not give reliable results when serum are icteric or lipemic or contain products of hemolysis, which are common in clinical samples. In chemiluminescence, there exists some inhibitors of chemiluminescence such as superoxide dismutase or N-nitro-L-arginine methyl ester hydrochloride whose presence requires reducing or eliminating these inhibitors before detection. Chromatography has its own problems. Chromatographic separation of the reaction mixture is more complex because of the presence of compounds with very similar chromatographic behavior with hydrophobicity and charge very different from each other. Optimizing test conditions is very important for the determination of both enzymes in a single serum sample.

Fluorescence and UV absorbance techniques also have problems. A large number of environmental factors including pH, ionic strength, noncovalent interactions, light intensity, temperature, and so on affect the results using these techniques. Strict reagent, vessel and equipment conditions are also required. If not, nonspecific fluorescence or fluorescence quenching may affect the results. Electrochemical techniques include detection using a gold electrode without modification, detection using a pyruvate oxidase modified electrode, detection using glutamate oxidase modified electrode, and detection using a L-lactate biosensor for GOT and GPT. Electrochemical measurements, however, tend to suffer from poor signal resolution against the interferent levels present in serum samples, which can be attributed both to the nature of the electrocatalytic surface and to relatively low protein loadings for enzyme immobilized at the electrode.

SUMMARY OF THE INVENTION

The most recent attempt to make a point-of-care transaminase test is described in work by the National Institutes of Health published in Clinical Gastroenterology and Hepatology, May 2013, titled "A point-of-care paper-based fingerstick transaminase test: towards low-cost "lab-on-a-chip" technology for the developing world," by Nira R. Pollock et al. The authors describe a 3D device made from layering patterned paper into a postage stamp-sized device that performs two separate tests on a single clinical sample in 15 minutes; one zone measures AST and another measure ALT. The device also contains three control zones to ensure proper device performance. The AST assay chemistry, which is based on the sulfonation of methyl green, results in a visual transformation from blue to pink. The ALT assay, which is based on peroxidase chemistry, generates a red dye in the presence of elevated ALT levels. However, this device is not yet available for clinical use.

Thus, there is a need for a point-of-care analyzer device that is capable of measuring liver enzymes and provides reliable and accurate results.

It is an object of the present invention to provide a point-of-care device and method for measuring liver enzyme levels in blood.

It is another object of the present invention to provide a point-of-care system and method for measuring liver enzyme levels in blood using an electrochemical technique.

It is further object of the present invention to provide a point-of-care system and method for measuring ALT and/or AST, and/or ALP, and/or GGT in blood.

It is an object of the present invention to provide a reliable and accurate result when using an electrochemical technique for the determination of ALT and/or AST, and/or ALP, and/or GGT in a blood sample.

The present invention achieves these and other objectives by providing, in one embodiment, a disposable test cartridge for a point-of-care system to determine the concentration of one or more liver enzymes in a blood sample.

In one embodiment of the present invention, the test cartridge includes a cartridge body, a removable cartridge cover and a test strip module. The cartridge body has a plurality of chambers where each of the plurality of chambers has an opening at a top of the cartridge body. At least one of the plurality of chambers contains a reactant mixture capable of undergoing a chemical reaction when combined with a blood sample forming a reaction solution containing at least one reaction product. The reactant mixture contains chemicals specific for being catalyzed by one of the liver enzymes ALT, AST, ALP, or GGT in the blood sample. The removable cartridge cover is removably connected to the cartridge body and covers the plurality of chambers. The removable cartridge cover also has a capillary-receiving aperture and a capillary element removably insertable into the cartridge cover. The capillary element extends into one of the plurality of chambers when the removable cartridge cover is connected to the cartridge body. The capillary element is configured for obtaining a blood sample by capillary action when the capillary element is touched to a blood sample. The test strip module is directly connected to the cartridge body and contains at least one analyte test strip configured for receiving a portion of the reaction solution and measuring at least one analyte where the at least one analyte is the at least one reaction product.

In another embodiment of the present invention, the reactant mixture containing chemicals specific to the determination of ALT includes L-alanine and α-ketoglutarate.

In another embodiment of the present invention, the reactant mixture containing chemicals specific to the determination of AST includes L-aspartate and α-ketoglutarate.

In another embodiment, the reactant mixture containing chemicals specific to the determination of AST includes L-aspartate, α-ketoglutarate and oxaloacetate decarboxylase.

In another embodiment, the reactant mixture containing chemicals specific to the determination of ALP includes sodium phenyl phosphate or its derivatives. The following reaction represents the chemical structure of the derivatives of the reactant, i.e. sodium phenyl phosphate, and the reaction product phenol and its derivatives.

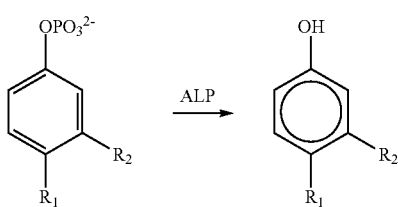

where $R_1$ and $R_2$ may be —H, —R, —OR, —$NO_2$, —COOR, —$SO_3H$, and the like. For the test data disclosed later, $R_1$ and $R_2$ are —H.

In another embodiment, the reactant mixture containing chemicals specific to the determination of GGT includes L-glutamic acid gamma-anilide and its derivatives and glycylglycine and its derivatives. The following reaction represents the chemical structure of the derivatives of the reactant, i.e. L-glutamic acid gamma-analide, and the reaction product analine and its derivatives.

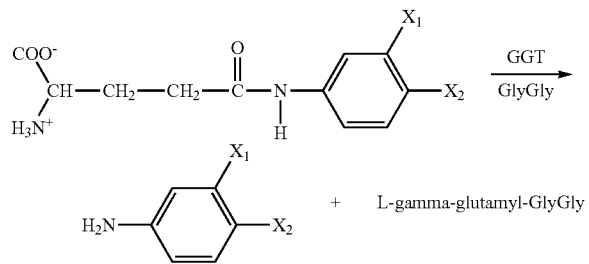

where $X_1$ and $X_2$ may be —H, —R, —OR, —$NO_2$, —COOR, —$SO_3H$, and the like.

In another embodiment, the test strip module incorporates an analyte test strip configured for measuring pyruvate or L-glutamate when the at least one of the plurality of chambers contains chemicals specific for being catalyzed by one of the liver enzymes ALT or AST.

In another embodiment, the test strip module incorporates an analyte test strip configured for measuring phenol or its derivatives when the at least one of the plurality of chambers contains chemicals that are catalyzed by the liver enzyme ALP.

In another embodiment, the test strip module incorporates an analyte test strip configured for measuring aniline or its derivatives when the at least one of the plurality of chambers contains chemicals that are catalyzed by the liver enzyme GGT.

In another embodiment, the test strip module incorporates an analyte test strip having a reagent matrix disposed on a working electrode containing one of pyruvate oxidase, glutamate oxidase or glutamate dehydrogenase.

In another embodiment, the test strip module incorporates an analyte test strip having a reagent matrix disposed on a working electrode that does not contain an enzyme or a mediator.

In another embodiment, the analyte test strip has an electrical contact end, a sample end and a sample receiving port spaced a predefined distance from the sample end.

In one embodiment, the sample end includes a vent opening and a sample channel between the sample receiving port and the vent opening.

In one embodiment, the test strip module incorporates two or more analyte test strips wherein at least two of the two or more analyte test strips measures the same analyte.

In one embodiment, the test strip module incorporates two or more analyte test strips wherein each of the two or more analyte test strips measures different analytes.

In one embodiment, a method for determining the concentration of one or more liver enzymes in a blood sample is disclosed. The method includes providing a blood sample receiving chamber, providing a reagent chamber containing predefined chemicals that are catalyzed by one of the liver enzymes ALT, AST, ALP, or GGT in the blood sample, obtaining a blood sample and placing at least a portion of the blood sample in the sample receiving chamber, diluting the blood sample forming a diluted blood sample, disposing a predefined amount of the diluted blood sample into the reagent chamber, allowing a reaction between the predefined chemicals and the diluted blood sample to continue for a predefined time period forming a reaction solution containing at least one reaction product, transferring a portion of the reaction solution to an analyte test strip capable of measuring an amount of the at least one reaction product in the reaction solution, measuring the amount of the at least one reaction product present in the reaction solution, and correlating the amount of the at least one reaction product in the reaction solution to the amount of one of the liver enzymes ALT, AST, ALP, or GGT in the blood sample.

In one embodiment, the measuring step further includes measuring an amount of one of pyruvate, glutamate, phenol (or its derivatives), or aniline (or its derivatives) in the reaction solution.

In one embodiment, the correlating step further includes correlating the amount of one of pyruvate, glutamate, phenol, or aniline in the reaction solution to the amount of ALT, AST, ALP, or GGT in the blood sample.

In one embodiment, the measuring step further includes using an electrochemical measurement technique to measure the at least one reaction product.

In one embodiment, the measuring step further includes using amperometry to measure the at least one reaction product for the determination of ALT, AST, ALP, or GGT.

In one embodiment, the measuring step includes using linear sweep voltammetry to measure the at least one reaction product for the determination of ALP.

In another embodiment, a disposable test cartridge kit for use in a point-of-care analyzer to determine the concentration of one or more liver enzymes in a blood sample is disclosed. The kit includes a cartridge body, a removable cartridge cover and a test strip module. The cartridge body has a plurality of chambers where each of the plurality of chambers has an opening at a top of the cartridge body. At least one of the plurality of chambers contains a reactant mixture capable of undergoing a chemical reaction when combined with a blood sample forming a reaction solution containing at least one reaction product. The reactant mixture contains chemicals specific for being catalyzed by one of the liver enzymes ALT, AST, ALP, or GGT in the blood sample. A disposable pipette tip is disposed in another of the plurality of chambers. The removable cartridge cover is removably connected to the cartridge body and covers the plurality of chambers. The removable cartridge cover also has a capillary-receiving aperture and a capillary element removably insertable into the cartridge cover. The capillary element extends into one of the plurality of chambers when the removable cartridge cover is connected to the cartridge body. The capillary element is configured for obtaining a blood sample by capillary action when the capillary element is removed from the disposable test cartridge and touched to a blood sample. The test strip module is directly connected to the cartridge body and contains at least one analyte test strip configured for receiving a portion of the reaction solution and measuring at least one analyte where the at least one analyte is the at least one reaction product.

In another embodiment, the kit includes instructions on the use of the disposable test cartridge and use of the capillary element.

BRIEF DESCRIPTION OF THE DRAWINGS

FIG. 7 is a top plan view of the cartridge body of the disposable test cartridge of FIG. 1.

FIG. 8 is an enlarged cross-sectional view of the sensor module taken along line A-A in FIG. 7.

FIG. 9 is an enlarged cross-sectional view of the sensor module taken along line B-B in FIG. 7.

FIG. 10 is a front, left side perspective view of the cartridge body of the disposable cartridge of FIG. 1.

FIG. 11 is an enlarged view of the area delineated by rectangle D of FIG. 10.

FIG. 21 is a graphic representation of a linear scan (i.e. sweep) voltammogram response for ALP current versus volts using the current sensor of FIG. 20 a.

DETAILED DESCRIPTION OF THE INVENTION

Figure 1:
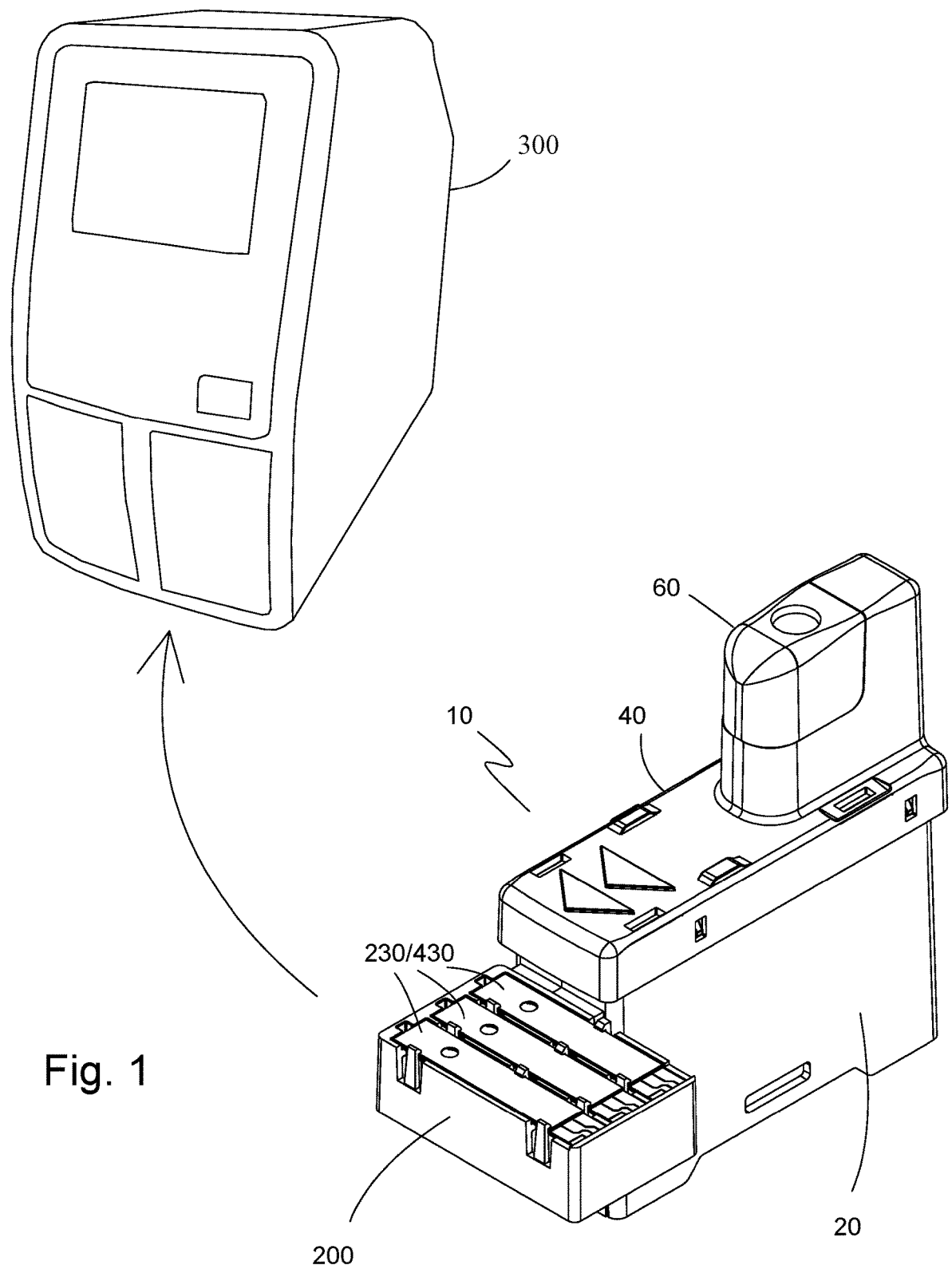
FIG. 1 is a perspective view of one embodiment of the present invention showing a point-of-care analyzer and a disposable test cartridge for the point-of-care analyzer.

FIG. 1 shows one embodiment of a disposable test cartridge 10 for use in a point-of-care analyzer 300 for determination of various liver enzymes. Test cartridge 10 includes a cartridge body 20, a cartridge cover 40, a capillary element 60, a capillary wiper 80 (not shown), and a test strip module 200 having one or more analyte test strips 230, 430. Capillary element 60 is removable from the cartridge cover 40.

Figure 2:
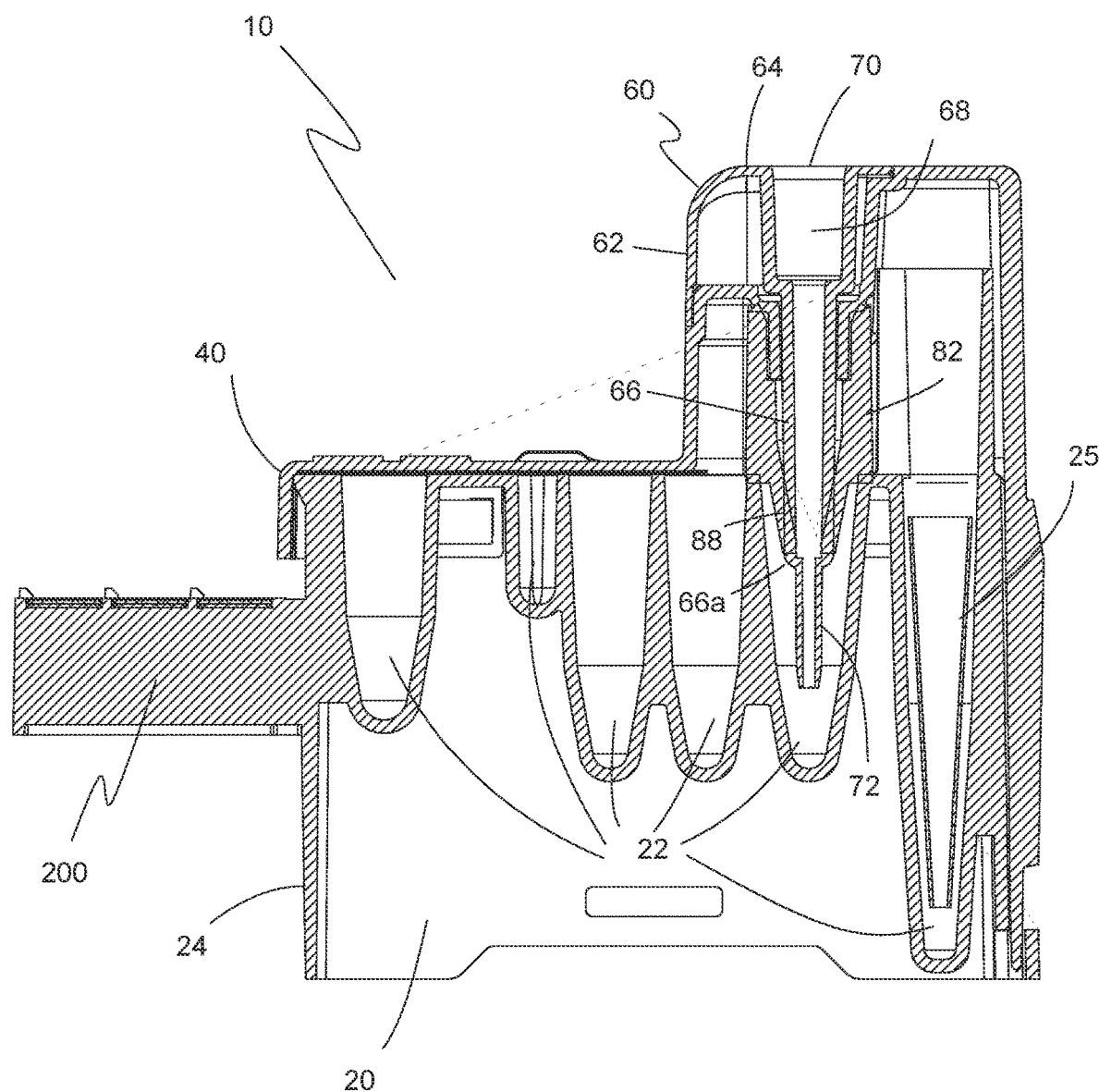
FIG. 2 is an enlarged, cross-sectional view of the disposable test cartridge of FIG. 1 showing the test strip module, the capillary wiper and the disposable pipette tip.

Turning now to FIG. 2, there is illustrated a cross-sectional view of the disposable test cartridge 10 showing the capillary element 60, the capillary wiper 80, the cartridge cover 40, and the test strip module 200. Capillary element 60 includes a capillary element body 62 having a top body surface 64, a depending capillary element finger 66 defining a capillary element volume 68, a top body opening 70 that communicates with capillary element volume 68, and a capillary tube 72 extending from a finger end 66a. Capillary element volume 68 decreases in cross-sectional area from top body opening 70 to finger end 66a. It is understood that capillary element volume 68 is open and continuous from top body opening 70 and through capillary tube 72. Capillary element volume 68 may have a continuous taper or a stepped taper or a plurality of concentric, reduced diameters. Capillary wiper 80 has an upper portion 82 and a tapered lower portion 88. As can be seen, capillary tube 72 extends through tapered lower portion 88 of capillary wiper 80 and into one of a plurality of chambers 22 within cartridge body 20. Test strip module 200 is connected to cartridge body 20. In this embodiment, test strip module 200 is connected to a front wall 24 of cartridge body 20. Test strip module 200 may be physically connected by fasteners, adhesive coatings, interlocking structure, and the like, or it may be molded as part of cartridge body 20 forming a unitary structure. It is contemplated that test strip module 200 may also be connected along the side of cartridge body 20.

Figures 3, 4:
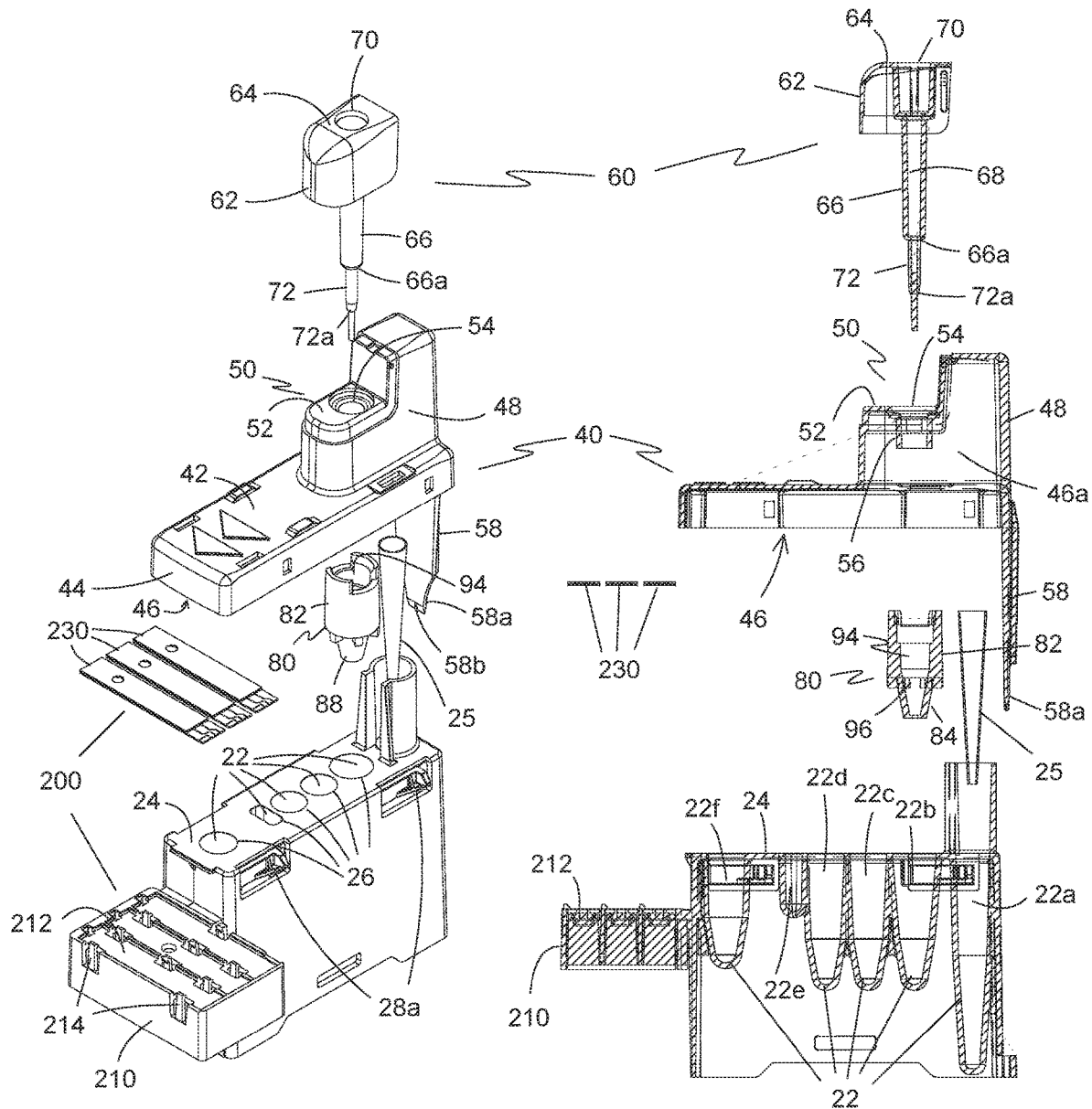
FIG. 3 is an exploded perspective view of the disposable test cartridge of FIG. 1.
FIG. 4 is an exploded side view of the disposable test cartridge of FIG. 1.

FIGS. 3 and 4 are exploded views of disposable test cartridge 10 shown in FIG. 1. FIG. 3 is a front perspective view and FIG. 4 is a side cross-sectional view of test cartridge 10. Cartridge body 20 has a plurality of chambers 22 extending below a cartridge body top surface 24, each having an opening 26. The plurality of chambers 22 are aligned in a row, one behind the other, between a cartridge body front wall 24 and a cartridge body rear wall 23. This arrangement, however, is not critical. Each of the plurality of chambers 22 has a specific purpose such as receiving the test sample, holding a chemical reagent adapted for a specific test, one or more calibration standards, a solution for diluting a blood sample, and the like. For example, disposable test cartridge 10 in combination with the point-of-care analyzer may provide test results that include, but are not limited to, ALT, AST, ALP, GGT, HbA1C, eAG, total cholesterol, HDL cholesterol, triglycerides, LDL cholesterol, cholesterol/HDL ratio, non-HDL cholesterol, urine albumin, urine creatinine, and albumin/creatinine ratio. More specifically and referencing FIG. 4, the plurality of chambers 22 of the cartridge body 20 are arranged in the following order. Chamber 22a contains a disposable pipette tip 25, chamber 22b is the sample receiving chamber into which capillary tube is inserted and the blood sample deposited. It is also the chamber where the blood sample is diluted. Chamber 22c to 22e contain various reagents for determining a predefined set of test results, and chamber 22f typically contains a buffer solution or other salt solution for diluting the blood sample deposited in chamber 22b. Not shown in FIGS. 3 and 4 is a foil seal that covers all of the openings 26 of the plurality of chambers 22 to prevent contamination of the chambers 22 and contamination of reagents contained within some of the chambers.

Capillary wiper 80 has upper portion 82 and tapered lower portion 88. Upper portion 82 and tapered lower portion 88 are tubular, meaning that capillary wiper 80 defines a capillary wiper volume 94. A lower volume portion 96 is adapted to receive a portion of capillary finger element 66 and capillary tube 72.

Cartridge cover 40 has a cover top surface 42 with a plurality of descending cover sides 44 forming a cover recess 46. Extending upward from cover top surface 42 is cover extension 48 that also forms a recess portion 46a of cover recess 46. Cover extension 48 has a stepped extension portion 50 with an extension portion top surface 52 and a capillary-receiving aperture 54 that communicates with portion 46a of cover recess 46. A cover tube extension 56 extends a predefined distance from capillary-receiving aperture 54 into recess portion 46a. Cover tube extension 56 mates with upper portion 82 of capillary wiper 80. Cover recess 46 receives a top portion 28 of cartridge body 20 and is locked in place with releasable tabs 28a. Cartridge cover 40, in this embodiment, also has a backside extension 58 with a back extension end 58a. Back side extension 58 extends along and adjacent to cartridge body rear wall 23 and back extension end 58a is received within a cover receiving slot 29 located on cartridge body 20. Back extension end 58a has a small sharp point 58b (more clearly shown in FIG. 3) that is used by the point-of-care analyzer 300 to pierce the foil covered openings 26 of the plurality of chambers 22 during use of the disposable test cartridge 10. The pipette tip 25 is used by the analyzer 300 to dilute the sample and select a predefined quantity of the diluted sample for mixing with the test reagents forming a test product after the test reagents react for a predefined time period with the diluted blood sample. The pipette tip 25 is also used for removing a predefined quantity of the test product for subsequent measurement by one or more of the analyte strips 230, 430 (shown in FIGS. 13-14) of the strip module 200. It is understood that the analyzer removes cartridge cover 40 and uses the back extension end 58a to pierce the foil seal once the capillary tube 72 and sample are inserted into and assembled with cartridge cover 40 and then the disposable test cartridge 10 is inserted into the analyzer 200.

As previously discussed, capillary element 60 has element body 62, top body surface 64, depending capillary element finger 66 defining a capillary element volume 68, top body opening 70 that communicates with capillary element volume 68, and a capillary tube 72 extending from a finger end 66a. Capillary tube 72 has a tube distal end 72a that may optionally be tapered.

Sensor strip module 200 includes a module body 210 and the one or more analyte sensor strips 230. The one or more analyte sensor strips 230 are single-use and disposable. Module body 210 includes a module body platform 212 for receiving one or more analyte sensor strips 230 and a plurality of retaining devices 214 that captures and retains the one or more analyte sensor strips 230 in a corresponding strip receiving area 224 on body platform 212.

Figure 5:
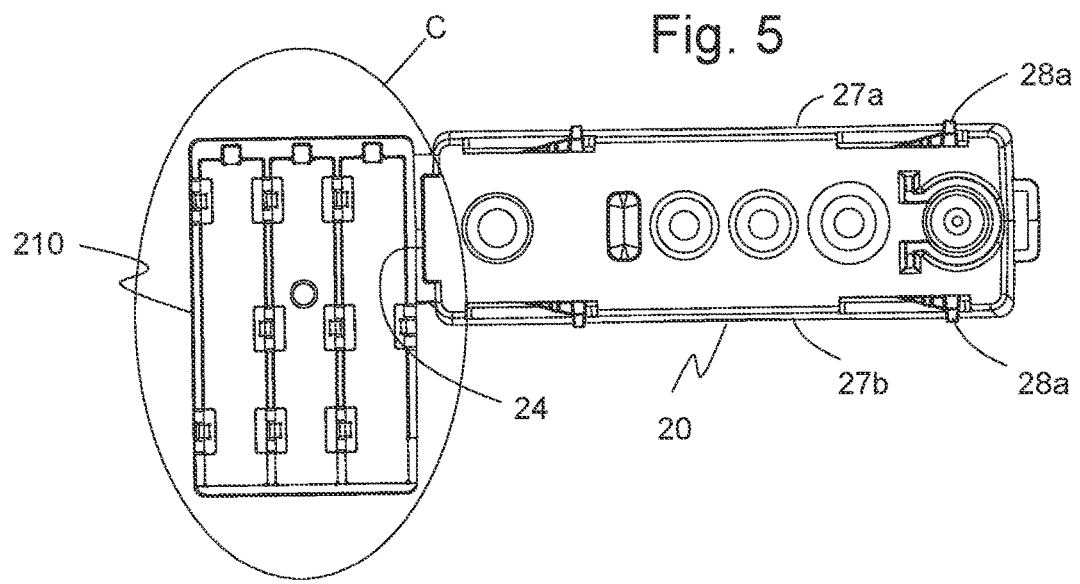
FIG. 5 is a top plan view of the cartridge body of the disposable test cartridge of FIG. 1.
Figure 6:
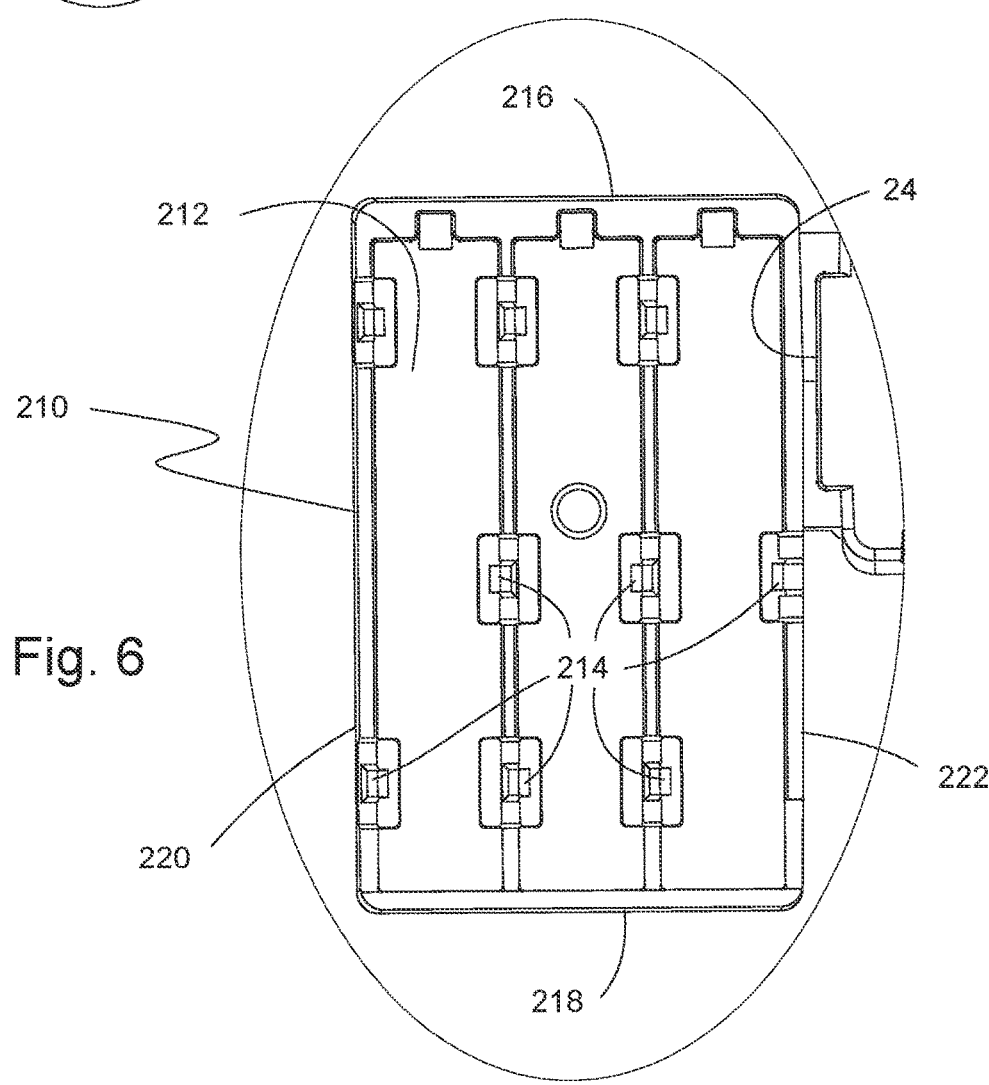
FIG. 6 is an enlarged view of the delineated area C of FIG. 5.

Turning now to FIG. 5, there is illustrated a top view of cartridge body 20 and strip module body 210. In this embodiment, releasable tabs 28a are shown as being located on opposite side walls 27a, 27b of cartridge body 20, which lock cover 40 in place after assembly of cover 40 to cartridge body 20. Releasable tabs 28a function to allow the point-of-care analyzer 300 to remove cover 40 from test cartridge 10 once test cartridge 10 is inserted into analyzer 300 for testing a blood sample previously deposited into a chamber 22 before insertion of test cartridge 10 and also to allow re-attachment of cover 40 after the testing is complete for removal and disposal of the test cartridge 10. In this embodiment, strip module body 210 is connected to cartridge front wall 24 of cartridge body 20 adjacent a first strip module wall 216 of strip module body 210. FIG. 6 is an enlarged view of the area delineated by oval C in FIG. 5. In this embodiment, strip module body 210 has first strip module wall 216, a second strip module wall 218, a module front wall 220, a module rear wall 222, module body platform 212 and a plurality of strip retaining devices 214. In this illustration, module body platform 212 is divided into three areas. Each of the three areas is configured to receive and retain an analyte test strip. Thus, in this embodiment, strip module body 210 is capable of retaining three analyte test strips for indirectly measuring ALT and/or AST and/or ALP and/or GGT in a blood sample.

FIG. 7 is a top plan view of cartridge body 20 and strip module body 210. In this view of cartridge body 20, there is shown the plurality of chambers 22, first cartridge body wall 27a, second cartridge body wall 27b, a plurality of cover retaining tabs 28a, cartridge body front wall 24, first strip module wall 216, second strip module wall 218, a front strip module wall 211a, a rear strip module wall 211b, and module body view lines A and B. FIG. 8 is an enlarged cross-sectional view of strip module body 210 taken along view line A-A in FIG. 7. As can be more clearly seen, module body platform 212 is recessed from a top strip module surface 210a and strip retaining devices 214 have hooked ends 214a adapted to receive a longitudinal edge 236 of analyte sensor strip 230. Module body platform 212 also includes a plurality of platform openings 212a through which a corresponding one of the plurality of strip retaining devices 214 extends above module body platform 212. FIG. 9 is an enlarged cross-sectional view of strip module body 210 taken along view line B-B in FIG. 7. It should be noted that the hooked ends 214a of the plurality of strip retaining devices 214 in this view face in an opposite direction when compared to the hooked ends 214a shown in FIG. 8. This is provided so that both opposing longitudinal edges 236 of analyte sensor strip 230 (shown in FIGS. 12-13) are secured to module body platform 212 within strip receiving area 224. It is contemplated that one side of each of the strip receiving areas 224 may have a ledge (not shown) that captures a portion of one longitudinal edge 236 of analyte sensor strip 230 while one or more strip retaining devices 214 captures a portion of the opposite longitudinal edge 236.

FIG. 10 is a perspective front view of cartridge body 20 and FIG. 11 is an enlarged perspective view of the area C delineated in FIG. 10. FIG. 11 more clearly shows the strip retaining device 214 extending through platform opening 212a and the hooked end 214a above recessed body platform 212. All of the plurality of strip retaining devices 214 are resilient to allow limited bending when inserting an analyte sensor strip 230 into strip receiving area 224 such that each strip retaining device 214 returns to its initial position capturing the analyte sensor strip 230 against module body platform 212 within strip receiving area 224.

Sensor Construction

Figure 12:
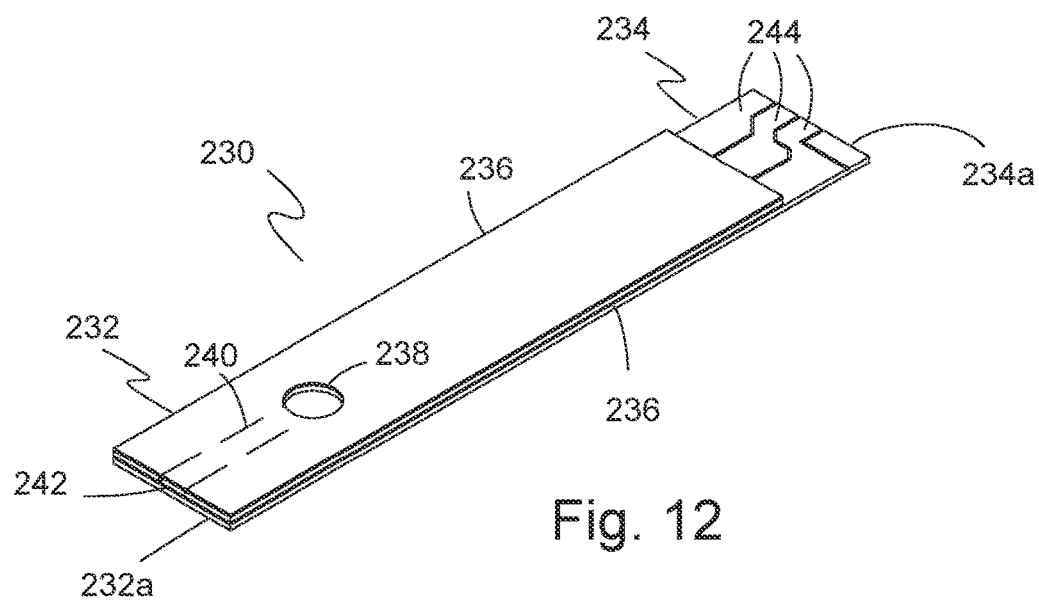
FIG. 12 is an enlarged, front perspective view of one embodiment of an analyte sensor strip of the disposable cartridge shown in FIG. 1.
Figure 13:
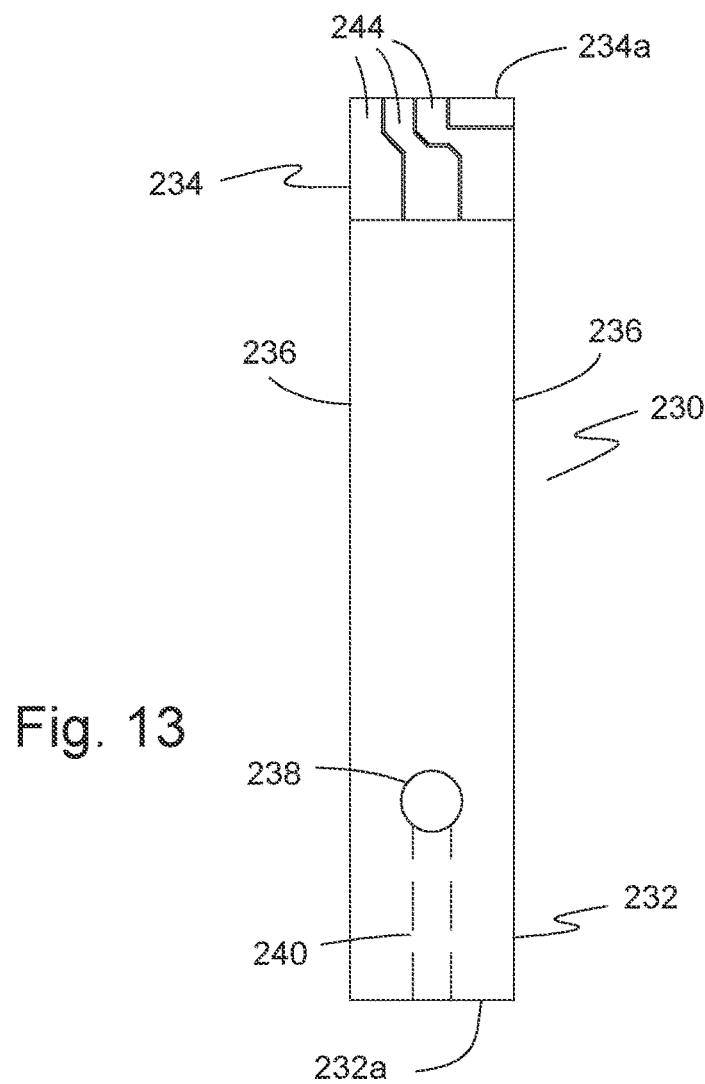
FIG. 13 is an enlarged, top plan view of the analyte sensor strip shown in FIG. 12.

Turning now to FIGS. 12 and 13, there is illustrated one embodiment of analyte sensor strip 230. Analyte sensor strip 230 is a multi-layered, integral sensor strip having an electrode end portion 232, an electrode end 232a, electrical contact end portion 234, an electrical contact end 234a, and opposite longitudinal edges 236. In this embodiment, electrode end portion 232 includes a sample inlet 238 for receiving a portion of the reaction solution, a strip test chamber 240, and a vent opening 242. Electrical contact end portion 234 has two or more electrical coupling pads 244 that are in electrical contact with respective electrodes situated within strip test chamber 240. In this embodiment, analyte sensor strip has a length of about 30.2 mm (1.1 inches) and a width of about 5.5 mm (0.22 inches).

Figure 14:
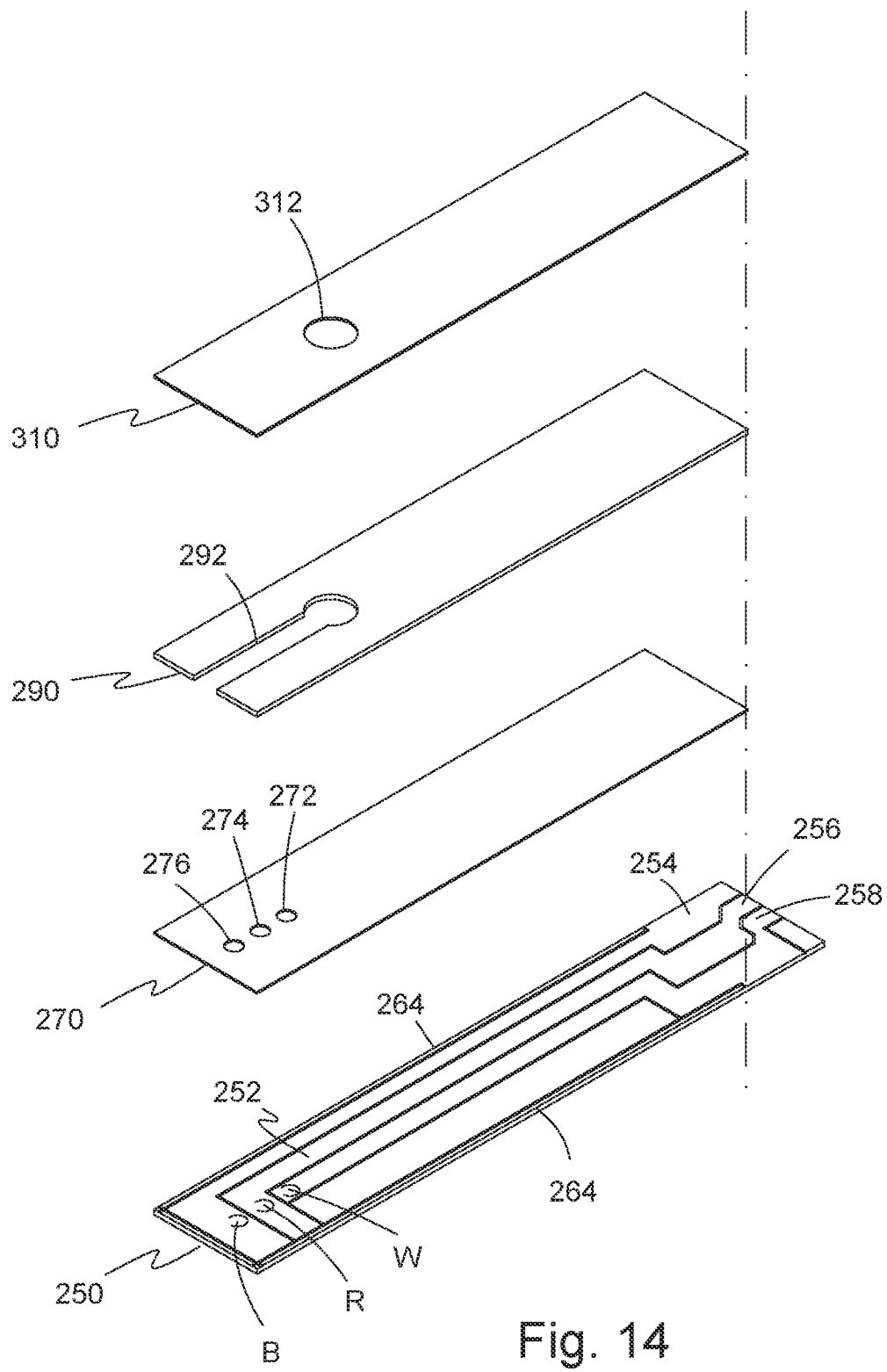
FIG. 14 is an exploded, perspective view of the analyte sensor strip shown in FIG. 12.

FIG. 14 is an enlarged, exploded, perspective view of the embodiment of analyte sensor strip 230 of FIGS. 12 and 13. As shown, the integral sensor strip of this embodiment has four strip layers. Analyte sensor strip 230 includes a base layer 250, an insulating and electrode delineating layer 270, a channel-forming layer 290, and a cover layer 310. All layers of analyte sensor strip 230 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, and polystyrene.

Base layer 250 has a conductive layer 252 on which is delineated three conductive paths 254, 256 and 258. The conductive paths 254, 256 and 258 may be formed by scribing or scoring conductive layer 252. In the alternative, base layer 250 may be a dielectric material on which conductive paths 254, 256 and 258 are silk screened. A piece of a gold polyester film may be used and cut to shape as illustrated in FIG. 14, forming base layer 250 of analyte sensor strip 230.

Scribing or scoring of conductive layer 252 may be done by mechanically scribing the conductive layer 252 sufficiently to create the at least two independent conductive paths 254, 256 and, optionally, a third conductive path 258. The preferred scribing or scoring method of the present invention is done by using a carbon dioxide laser, a YAG laser or an excimer laser. The scoring line is very thin but sufficient to create two or more separate electrical paths. Conductive layer 252 may be made of any electrically conductive material such as, for example, gold, tin oxide/gold, palladium, other noble metals or their oxides, or carbon film compositions. The preferred electrically conductive material is gold or tin oxide/gold. An additional scoring line 264 (enlarged and not to scale; for illustrative purposes only) may be made along the outer edge of base layer 250 in order to avoid possible static problems that could give rise to a noisy signal. It should be understood, however, that scoring line 264 is not necessary to the functionality of analyte sensor strip 230.

Strip insulating and electrode delineating layer 270 (also called reagent holding layer 270) has a first electrode opening 272 which exposes a portion of first conductive path 258, a second electrode opening 274 which exposes a portion of second conductive path 256, and, optionally, a third electrode opening 276 which exposes a portion of third conductive path 254. As illustrated in FIG. 14, electrode openings 272, 274 and 276 are aligned with each other and have a spacing of about 0.03 in. (0.64 mm) between adjacent openings but the spacing is not critical. The circular openings are for illustrative purposes only. It should be understood that the shape and size of the openings is not critical. The circular openings do not have to be substantially equal in size so long as the ratio of the surface areas remains substantially constant.

Reagent holding layer 270 is made of a plastic material, preferably a medical grade, one-sided adhesive tape available from Adhesive Research, Inc., of Glen Rock, PA or Global Instrument Corporation (GIC) (Taiwan). Acceptable thicknesses of the tape for use in the present invention are in the range of about 0.001 in. (0.025 mm) to about 0.005 in. (0.13 mm). The preferred thickness is about 0.003 in. (0.075 mm). It should be understood that the use of a tape is not required. Reagent holding layer 270 may be made from a plastic sheet and may be coated with a pressure sensitive adhesive, a photopolymer, ultrasonically-bonded to base layer 250, silk-screened onto the base layer 250, or 3D printed onto base layer 250 to achieve the same results as using the polyester tape mentioned.

The three electrode openings 272, 274 and 276 define electrode wells W, R and B, respectively, and hold chemical reagents forming a working electrode (W), a reference electrode (R), and a blank electrode (B). For the determination of ALT and AST, electrode well W is loaded with an enzyme capable of catalyzing a reaction involving a substrate for the enzyme or a substrate catalytically reactive with the enzyme and a mediator capable of transferring electrons transferred between the enzyme-catalyzed reaction and the working electrode to create a current representative of the activity of the enzyme or substrate (which is representative of the liver enzyme to be measured), and at least a polymer binder. Substrate electrode well B is loaded with a similar chemistry to electrode well W, but without the enzyme. One or more chemical components such as additional polymers, stabilizers, and bulking agents may be optionally included in the reagent matrix. A reference reagent matrix is loaded in electrode well R.

For the determination of ALP or GGT, electrode well W is not loaded with an enzyme or a mediator for reasons to be discussed later. It other words, electrode well W contains no enzyme and no mediator for the determination of ALP or GGT.

Preferably, the reference matrix contains at least a chemically oxidizing reagent such as a reduced form of a redox mediator, an oxidized form of a redox mediator, or a mixture of a reduced and an oxidized form of a redox mediator. For example, potassium ferricyanide, or potassium ferrocyanide, or a mixture of potassium ferricyanide and potassium ferrocyanide may be loaded to make the reference electrode function when using the preferred conductive coating material. The mixture of potassium ferricyanide and potassium ferrocyanide may be prepared such that the potassium ferricyanide concentration is in the range of up to about 10%, while the potassium ferrocyanide concentration is in the range of up to about 5%. In the alternative, the reference electrode (electrode well R) may be loaded with a Ag/AgCl layer (e.g., by applying Ag/AgCl ink or by sputter-coating (a) a Ag layer followed by chloridizing the Ag or (b) a Ag/AgCl layer) or other reference electrode materials that do not require a redox mediator to function properly. It should be noted that the positional arrangement of the working, the reference and the blank electrodes in the channel is not critical for obtaining usable results from the sensor.

Channel-forming layer 290 has a channel notch 292 located at electrode end portion 232. The length of channel notch 292 is such that when channel-forming layer 40 is laminated to reagent holding layer 270, electrode areas W, R and B are within the space defined by channel notch 292. The length, width and thickness of the channel notch 292 define the capillary chamber volume. Channel-forming layer 290 is laminated to insulating and electrode delineating layer 270. Like insulating and electrode delineating layer 270, channel-forming layer 290 may be made from a plastic sheet and may be coated with a pressure sensitive adhesive, a photopolymer, ultrasonically-bonded to insulating and electrode delineating layer 270, silk-screened onto the insulating and electrode delineating layer 270, or 3D printed onto insulating and electrode delineating layer 270.

Channel-forming layer 290 is made of a plastic material, preferably a medical grade, double-sided pressure-sensitive adhesive tape available from Adhesive Research, Inc., of Glen Rock, PA or Global Instrument Corporation (Taiwan). The thickness of the tape is preferably in the range of about 0.001 in. (0.025 mm) to about 0.010 in. (0.25 mm). Channel notch 292 can be made with a laser or by die-cutting (the preferred method). The length of channel notch 292 not including the fluid sample opening 312 is about 0.22 in. (5.68 mm) to about 0.250 in. (6.35 mm), the width is about 0.05 in. (1.28 mm) to about 0.07 in. (1.778 mm) and the thickness is about 0.0039 in. (0.1 mm) to about 0.009 in. (0.225 mm). It should be understood that the thickness and the size of channel notch 292 are not critical.

Cover layer 310, which is laminated to channel-forming layer 290, has a fluid sample opening 312 spaced from electrode end 232a of analyte sensor strip 230. Cover layer 310 forms vent opening 242 at electrode end 232a to ensure that the sample in the strip test chamber 240 will completely cover electrode areas W, R and B when the reaction product sample is disposed into fluid sample opening 312. The preferred material for cover 310 is a polyester film. In order to facilitate capillary action of the sample fluid within the test chamber 240, it is desirable for the polyester film to have a highly hydrophilic surface on that portion of the polyester film that forms the strip test chamber 240. Transparency films from 3M or from GIC may be used.

Figure 15:
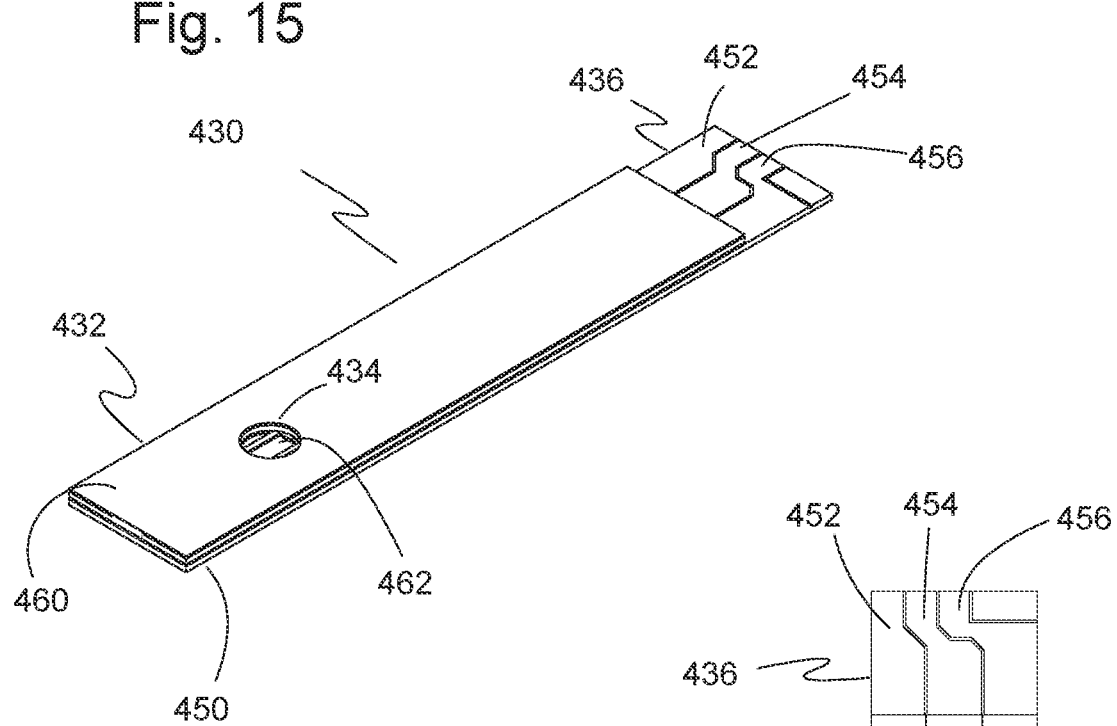
FIG. 15 is an enlarged, perspective view of another embodiment of an analyte sensor strip of the disposable test cartridge.
Figure 16:
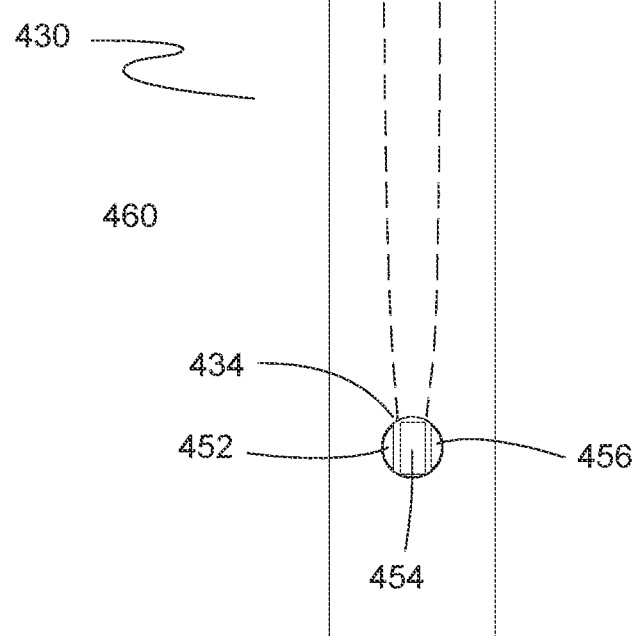
FIG. 16 is an enlarged, top plan view of the analyte sensor strip shown in FIG. 15.

Turning now to FIGS. 15 and 16, there is illustrated another embodiment of the analyte sensor strip 430. In this embodiment, analyte sensor strip 430 has a laminated body 432, a sample receiving well 434 and an electrical contact end 436. Laminated body 432 has a base layer 450 and a cover 460. Cover 460 has a sample opening 462 that forms, when combined with base layer 450, sample receiving well 434. Base layer 450 has at least three electrical paths 452, 454 and 456, which have a first portion exposed at electrical contact end 436 for connection to a sensor measuring device or module (not shown) and a second portion exposed by sample receiving well 434. It is understood that the layout of the scribed electrical paths in this embodiment (analyte test strip 430) is modified from the electrical paths in the previously disclosed embodiment (analyte test strip 230) to accommodate the three electrode areas W, R and B in the sample receiving well 464. An example of such an arrangement is shown in FIG. 16 by the dashed lines delineating one embodiment.

The second portion of electrical paths 452, 454 and 456 exposed by sample receiving well 434 create at least a working electrode W, a reference/counter electrode R, and an optional blank electrode B. As stated above for the determination of ALT and AST, a first reagent matrix 460 contains an enzyme capable of catalyzing a reaction involving a substrate for the enzyme or a substrate catalytically reactive with the enzyme, a mediator capable of transferring electrons transferred between the enzyme-catalyzed reaction and the working electrode to create a current representative of the activity of the enzyme or substrate (which is representative of the liver enzyme to be measured), and at least a polymer binder, and is disposed on the working electrode W. A second reagent matrix 462 is disposed on the optional blank electrode B and contains a similar chemistry to electrode well W, but without the enzyme and mediator. As previously stated, one or more chemical components such as additional polymers, stabilizers, and bulking agents may be optionally included in the reagent matrix. The reference/counter electrode R may contain any reference material previously disclosed.

For the determination of ALP or GGT, electrode well W is not loaded with an enzyme or a mediator for reasons to be discussed later.

In this embodiment of the present invention, sample receiving well 434 serves as both the sample inlet and the sample chamber for receiving the reaction product.

It should be understood that the conduit paths in any of the embodiments disclosed herein may be made from any non-corroding metal. Carbon deposits such as for example carbon paste or carbon ink may also be used as the conduit paths, all as is well known by those of ordinary skill in the art. It is further understood that when a blank electrode B is optionally included in analyte sensor strips 230, 430, for the determination of ALT or AST, it is used for correcting any current created by interferents in the blood sample. For the determination of ALP or GGT, it is used primarily to determine any malfunction in the sample flowing into the test chamber.

Chemical Reagents for Analyte Test Strips for Determination of ALT or AST

Enzyme

The analyte test strip 230 of the present invention includes at least a chemical agent in the reagent matrix of the working electrode W that consumes either pyruvate or glutamate depending on the enzyme used in the reagent matrix. The chemical agent is one of pyruvate oxidase, which can selectively react with the pyruvate present in the reaction solution developed in test cartridge 10 during use, or glutamate oxidase or glutamate dehydrogenase, which can selectively react with the L-glutamate present in the reaction solution developed in test cartridge 10 during use. The blank electrode B is not necessary in the present invention and the sensor strip 230, 430 may only have electrode W and electrode R. Blank electrode B may optionally be included for the elimination of electrical background current potentially caused by possible interferent chemical species in the blood sample. As previously explained, the use of such a blank electrode B helps to better distinguish the current caused by either pyruvate or L-glutamate in conjunction with the mediator, as the case may be, from the current caused by other oxidizable species in the reaction product. A commercially available pyruvate oxidase is available from various sources including, but not limited to, Sigma-Aldrich now known as MilliporeSigma, AG Scientific, Inc., Sekisui Diagnostics, and Toyoba USA, Inc. A commercially available L-glutamate oxidase is available from various sources including, but not limited to, Sigma-Aldrich, Cosmo Bio USA, and Sorachim SA. A commercially available glutamate dehydrogenase is available from various sources including, but not limited to, Sigma-Aldrich, MyBioSource-.com, Lee Biosolutions, Inc., and BBI Solutions. The concentration of these chemical agents in the reagent matrix for the sensor strip is in the range of about 0.1% to 10%, and preferably, 0.5% to 2%.

Chemically Oxidizing Reagents

Chemically oxidizing reagents such as redox mediators are included in the reagent matrix of the working electrode W, the optional blank electrode B and in the reference electrode R unless the reference electrode R is one that doesn't require a chemically oxidizing reagent such as, for example, a Ag-AgCl reference electrode. When using a redox mediator, it is preferable to use the redox mediator in its oxidized form. It is also desirable that the reduced form of the mediator is capable of being oxidized electrochemically at the electrode surface at the applied potential. It is further desirable that the mediator is stable in the reagent matrix. When used in a reference electrode, it is still further desirable that the mediator can make the reference electrode function properly. The redox mediator can be selected from, but not limited to, various metal compounds and organic redox compounds. Examples of acceptable redox mediators include, but are not limited to, various metal compounds and organic redox compounds. Examples of acceptable redox mediators include potassium (or sodium) ferricyanide, ferrocene and its derivatives, ruthenium compounds such as hexaammineruthenium (III) chloride and its derivatives, and osmium complexes, 1,10-phenanthroline-5,6-dione, meldola's blue, Tetrathiafulvalene 7,7.8.8-tetracyanoquinodimethane, Tetrathiafulvalene, TCNQ, hydroquinone, dichlorophenoliondophenol, p-benoquinone, o-phenylenediamine, 3,4-dihydroxybenzaldehyde, indophenols, phenazines, phenothiazine, 2,6-dichloroindophenol, toluidine blue O et. al. The preferred mediator is 1,10-phenanthroline-5,6-dione. The concentration of 1,10-phenanthroline-5,6-dione in the reagent matrix is preferably about 0.1% to about 5% (w/w) of the reagent matrix and preferably about 0.1% to 0.5%.

Enzyme Co-Factors

The enzyme co-factors included in the reagent matrix of the analyte sensor strip 230, 430 are the organic cofactors thiamine triphosphate (TPP) and flavin adenine dinucleotide (FAD), and the inorganic co-factor $Mg^{2+}$ if pyruvate oxidase is used. Co-factor of NAD is used if Glutamate dehydrogenase is used. The concentration of each co-factor in the reagent matrix is about 0.25% (w/w).

Polymer Binder

The polymer used as the binder in the reagent matrix should be sufficiently water-soluble and should also be capable of stabilizing and binding all other chemicals in the reagent to the conductive surface layer in the electrode area. Suitable polymers include, but are not limited to, low and high molecular weight polyethylene oxide (PEO), polyethylene glycol, polyvinyl pyrolidone, starch, methylcellulose, hydroxypropylcellulose, polyvinyl alcohol (PVA), carboxy methyl cellulose (CMC), and polyamino acids. The reagent binder may be a single polymer or a combination of polymers preferable in a concentration range of about 0.02% (w/w) to about 7.0% (w/w). The preferred binder in the reagent matrix of the present invention is a combination of polyethylene oxide (PEO) and methylcellulose. PEO's molecular weight ranges from thousands to millions and is available from Scientific Polymer Products, NY, USA. The concentration of PEO in the reagent matrix is preferably about 0.04% (w/w) to about 2% (w/w). Methylcellulose, which is available under the brand name of Methocel 60 HG (Cat. No. 64655, Fluka Chemicals, Milwaukee, WI, USA) has a concentration in the reagent matrix preferably in the range of about 0.02% (w/w) to about 5% (w/w).

Surfactants

A surfactant may be optionally included in the reagent matrix to facilitate dispensing of the reagent matrix into the electrode areas. The surfactant also helps in quickly dissolving the dry chemical reagents when a sample fluid enters the sample channel of the analyte test strip. The amount and type of surfactant is selected to assure the previously mentioned functions and to avoid a denaturing effect on the enzymes. Surfactants can be selected from, but are not limited to, various anionic, cationic, non-ionic, and zwitterionic detergents. Examples of acceptable surfactants are polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100. The concentration of surfactant in the reagent matrix is preferably about 0.01% (w/w) to about 2%.

Buffer

Optionally, a buffer may be present in dried form in the sensor strip of the present invention. The buffer is present in a sufficient amount so as to substantially maintain the pH of the reagent matrixs. Examples of suitable buffers include phosphate buffer, citrate buffer, TRIS buffer, and the like. The pH of the buffer is preferably in the range from about 5.0 to about 8.5.

Bulking Reagent

An optional bulking agent that is water soluble and an inactive ingredient is preferably added into the reagent mixture/matrix. The use of a bulking agent is advantageous when an electrode forming layer is used to contain the reagent matrix such that the electrode openings in the electrode forming layer will not trap bubbles when a sample fluid fills the capillary channel. Various sugars such as, for example, trehalose, galactose, glucose, sucrose, lactose, mannitol, mannose, fructose, sucrose, lactose, lactitol, sorbitol, xylitol, nicotinamide, maltose, and the like, can be added into the reagent mixture/matrix as long as they do not react with other ingredients and are inactive at the electrode surface. The bulking agent can be one chemical or a combination of chemicals. The amount of bulking agent in the reagent mixture/matrix when included is in the range from about 1% to about 15% (w/w).

Chemical Reagents for Analyte Test Strips for Determination of ALP or GGT

Polymer Binder, Surfactant, Bulking Reagent, but No Enzyme or Mediator

The polymer binder, surfactant and bulking reagent are the same ones listed above for the analyte test strips for the determination of ALT and AST. It is notable that no enzyme or mediator is used in the reagent matrix for the analyte sensor strips for the determination of ALP and GGT. This is so because the reaction product that is measured for ALP and GGT determination is directly oxidizable at the electrode surface and therefore does not need a substrate of the reaction product and a mediator to generate the current.

Buffer

A buffer is present in the reagent matrix for the analyte sensor strips for the determination of ALP and provides a pH range of 7 to 12. Preferably, the buffer provides a pH range of 10 to 11. Examples of such a buffer include diethanolamine buffer, AMP (2-Amino-2-methyl-1-propanol) buffer and the like.

A buffer is also present in the reagent matrix for the analyte sensor strips for the determination of GGT and provides a pH range of 7 to 9. Preferably, the buffer provides a pH of 8.3. Examples of such buffers include phosphate buffer, TRIS buffer, citric buffer and the like. The preferred buffer is TRIS buffer.

Chemical Reagents Disposed in a Chamber of the Disposable Test Cartridge For Determination of ALT, AST, ALP or GGT Reagents for ALT To measure the amount of the liver enzyme ALT in a blood sample, reagents are deposited in at least one of the plurality of chambers 22 of disposable test cartridge 10 forming a reactant mixture during assembly of the disposable test cartridge. For ALT, the chamber 22 includes the following reagents: L-alanine, α-ketoglutarate, a polymer binder, a surfactant, a buffer, a bulking agent such as a sugar, and a preservative.

The L-alanine concentration is in the range of 0.01 M to 2 M. The preferred concentration is in the range of 0.1 M to 1 M and a concentration in a range of 0.2 to 0.5 M is the most preferred. For the test data disclosed later, the concentration used is 0.3 M.

The α-ketoglutarate concentration is in the range from 0.01 to 2 M. The preferred concentration is in the range of 0.05 M to 1 M and a concentration in a range of 0.1 M to 0.5 M is most preferred. For the test disclosed later, the concentration used is 0.2 M.

The polymer used as the binder in the reactant mixture should be sufficiently water-soluble and should also be capable of stabilizing and binding all other chemicals in the reactant mixture. Suitable polymers include, but are not limited to, polyethylene oxide (PEO), polyethylene glycol, polyvinylpyrrolidone, starch, methylcellulose, hydroxypropylcellulose, polyvinyl alcohol (PVA), carboxy methyl cellulose (CMC), fish gelatin, Chitosan, gum and polyamino acids. The polymer binder may be a single polymer or a combination of polymers. For PEO, the molecular weight of the PEO ranges from thousands to millions and is available from Scientific Polymer Products, NY, USA. The concentration of PEO in the reactant mixture is preferably about 0.04% (w/w) to about 2%. Methylcellulose, which is available under the brand name of Methocel 60 HG (Cat. No. 64655, Fluka Chemicals, Milwaukee, WI, USA), has a concentration in the reagent layer composition preferably in the range of about 0.02% (w/w) to about 5%.

The surfactant is selected from, but is not limited to, various anionic, cationic, non-ionic, and zwitterionic detergents. Examples of acceptable surfactants are polyoxyethylene ether, Tween 20, sodium cholate hydrate, hexadecylpyridinium cholide monohydrate and CHAPS (which is a zwitterionic detergent). The preferred surfactant is a polyoxyethylene ether. More preferably, it is toctylphenoxypolyethoxyethanol and is available under the brand name Triton X-100. The concentration of Triton X-100 in the reactant mixture is preferably about 0.01% (w/w) to about 2%.

A buffer is added to the reactant mixture. A pH range of 5 to 11 is acceptable. The preferred range is a pH of 7 to 8. For the test data discloses later, a pH of 7.4 is used. Acceptable buffers for use in determination of ALT includes phosphate buffer, a trizma buffer, a citric buffer and the like.

An optional bulking agent that is water soluble and an inactive ingredient is preferably added into the reactant mixture. The use of a bulking agent is advantageous for reducing the tendency to trap bubbles in the reactant mixture once the blood sample is added to the chamber 22 containing the reactant mixture. Various sugars such as, for example, trehalose, galactose, sucrose, lactose, mannitol, mannose, fructose, lactitol, sorbitol, xylitol, nicotinamide, maltose, starch, and the like, may be added as a bulking agent into the reactant mixture so long as they do not react with other ingredients. The bulking agent may be one chemical or a combination of chemicals. The amount of bulking agent in the reactant mixture is in the range from about 1% to about 15% (w/w).

Because pre-assembled disposable cartridges are typically stored for months before use, the inclusion of at least one preservative is encouraged. The preservative provides long term stability of the reactant mixture in the pre-assembled disposable cartridge. A preservative such as Prolin (which is a proteinogenic amino acid) is included in the reactant mixture in a concentration in a range of 0.05% to 2%.

Reagents for AST

To measure the amount of the liver enzyme AST in a blood sample, reagents are deposited in at least one of the plurality of chambers 22 of disposable test cartridge 10 forming a reactant mixture during assembly of the disposable test cartridge. For AST, the chamber 22 includes the following reagents: L-aspartic acid, α-ketoglutarate, a polymer binder, a surfactant, a buffer, a bulking agent such as a sugar, a buffer, a preservative, and, optionally, oxaloacetate decarboxylase.

The L-aspartic acid concentration is in the range of 0.01 M to 2 M. The preferred concentration is in the range of 0.1 M to 1 M and a concentration in a range of 0.2 to 0.5 M is the most preferred. For the test data disclosed later, the concentration used is 0.5 M.

The α-ketoglutarate concentration is in the range from 0.01 to 2 M. The preferred concentration is in the range of 0.05 M to 1 M and a concentration in a range of 0.1 M to 0.5 M is most preferred. For the test disclosed later, the concentration used is 0.25 M.

The oxaloacetate decarboxylase concentration is in the range from 50 IU/mL to 500 IU/mL. For the test disclosed later, the concentration used is in the range from 100 IU/mL to 150 IU/mL.

The polymer binder, the surfactant, optional bulking agent, and the preservative are the same as those listed above for the determination of ALT.

A buffer is added to the reactant mixture. A pH range of 5 to 11 is acceptable. The preferred range is a pH of 7 to 9. For the test data disclosed later, a pH of 8 is used. Acceptable buffers for use in determination of ALT include phosphate buffer, a TRIS buffer, a citric buffer and the like.

Reagents for ALP

To measure the amount of the liver enzyme ALP in a blood sample, reagents are deposited in at least one of the plurality of chambers 22 of disposable test cartridge 10 forming a reactant mixture during assembly of the disposable test cartridge. For ALP, the chamber 22 includes the following reagents: Sodium phenyl phosphate or its derivatives, a polymer binder, a surfactant, a buffer, a bulking agent such as a sugar, a buffer, and a preservative.

The sodium phenyl phosphate concentration is in the range of 100 mM to 300 mM. For the test data disclosed later, the concentration used is 200 mM.

The polymer binder, the surfactant, optional bulking agent, and the preservative are the same as those listed above for the determination of ALT.

A buffer is added to the reactant mixture. A pH range of 7 to 12 is acceptable. The preferred range is a pH of 10 to 11. Acceptable buffers for use in determination of ALP includes diethanolamine buffer, AMP (2-Amino-2-methyl-1-propanol; buffer and the like.

Reagents for GGT

To measure the amount of the liver enzyme GGT in a blood sample, reagents are deposited in at least one of the plurality of chambers 22 of disposable test cartridge 10 forming a reactant mixture during assembly of the disposable test cartridge. For GGT, the chamber 22 includes the following reagents: L-glutamic acid gamma-anilide or its derivatives, glycylglycine, a polymer binder, a surfactant, a buffer, a bulking agent such as a sugar, a buffer, and a preservative.

The L-glutamic acid gamma-anilide concentration is in the range of 10 mM to 30 mM. For the test data disclosed later, the concentration used is 20 mM.

The glycylglycine concentration is in the range of 200 mM to 400 mM. For the test date disclosed later, the concentration used is 300 mM.

The polymer binder, the surfactant, optional bulking agent, and the preservative are the same as those listed above for the determination of ALT.

A buffer is added to the reactant mixture. A pH range of 5 to 11 is acceptable. The preferred range is a pH of 7 to 9. For the test data disclosed later, a pH of 8.3 is used. Acceptable buffers for use in determination of ALT include phosphate buffer, a TRIS buffer, a citric buffer and the like.

Generalized Procedure for the Determination of ALT, AST, ALP, and GGT in a Blood Sample The following generalized test procedure for the determination of certain liver enzymes is performed for the determination of a liver enzyme such as ALT, AST, ALP, and GGT. This test involves obtaining a predefined quantity of capillary blood, diluting the predefined quantity of capillary blood, pipetting a predefined quantity of the diluted capillary blood into a chamber 22 containing the reactant mixture for the determination of a particular liver enzyme, which diluted capillary blood re-suspends the reactant mixture, the diluted capillary blood mixes with the reactant mixture and the resultant mix of the diluted capillary blood and the reactant mixture is allowed to react for a predefined length of time forming a reaction solution. At the end of the predefined reaction time, a predefined quantity of the reaction solution is withdrawn by the pipette inside the point-of-care analyzer 300 and deposited onto the analyte test strip 230, 430 on test strip module 200 to measure the quantity of a particular analyte in the reaction solution the analyte test strip 230, 430 is capable of determining, which analyte is directly related to the determination of a particular liver enzyme.

More specifically, a blood sample is obtained using a lancet to lance a finger of a patient. A disposable test cartridge 10 is selected for the specific test to be performed. In this case, it is a disposable test cartridge 10 capable of testing for the presence of one of the four liver enzymes ALT, AST, ALP, and GGT. The specific test cartridge 10 has at least one analyte sensor strip 230, 430 attached to test strip module 200 for measuring an analyte. Each disposable test cartridge 10 is coded for the type of liver enzyme determination and the type of analyte sensor strip 230, 430.

The capillary element 60 is separated from disposable test cartridge 10. The finger end 66a of the capillary element finger 66 is touched to the blood droplet on the finger created as a result of lancing the patient's skin. A portion of the blood droplet enters capillary element 60 by capillary action. Capillary element 60 is inserted into and reattached to disposable test cartridge 10 in the same orientation that it was in when it was removed from disposable test cartridge 10 prior to obtaining the blood sample. Once re-attached, disposable test cartridge 20 is ready to be inserted into point-of-care analyzer 300. Once inserted, point-of-care analyzer 300 is started.

While in the point-of-care analyzer 300, the sample of capillary blood residing in capillary element 66 is aspirated by the analyzer 300 into the chamber 22 in which the capillary element 66 is suspended. Cover 40 is removed from disposable test cartridge 20 and a predefined quantity of a predefined diluent (i.e. buffer or salt solution) residing in a different chamber 22 of the disposable test cartridge 10 is removed and deposited into the chamber 22 containing the blood sample by a pipette. A sufficient amount of diluent is added to the chamber 22 containing the blood sample to obtain a dilution ratio in the range of 1:1 to 1:50. One preferred range of the dilution ratio is in the range of 1:2 to 1:20. The most preferred range of the dilution ratio for use in analyzer 300 is in the range of 1:5 to 1:10. For the test data shown, the dilution ratio used was 1:10. It is understood that the diluent is the larger number in the dilution ratio or it is equal to the amount of capillary blood in the chamber. After dilution, a predefined quantity of the diluted blood sample is pipetted into the chamber 22 of the disposable test cartridge 10 that contains the reactant mixture for determining a particular liver enzyme activity in the diluted blood sample. Although each disposable test cartridge 10 may be dedicated to only one liver enzyme, it is contemplated that a disposable test cartridge 10 may include tests for other liver enzymes disclosed herein. It is further contemplated that additional analyte test strips for the determination of the other liver enzymes would also be incorporated in a disposable test cartridge 10 that is configured to test for two or more of the liver enzymes in the blood sample.

Determination of ALT in a Blood Sample

In the presence of ALT as the catalyst, L-analine and α-ketoglutarate undergo a reaction that produces pyruvate and L-glutamate. This is represented by Equation 1:

$$L - \text{alanine} + \alpha - \text{ketoglutarate} \xrightarrow{ALT} \text{pyruvate} + L - \text{glutamate} \qquad \text{Eq. 1}$$

After dilution, a predefined quantity of the diluted blood sample is pipetted into the chamber 22 of the disposable test cartridge 10 that contains the reactant mixture for determining the ALT activity in the blood sample. The amount of the predefined quantity of diluted blood sample is in the range of 5 to 100 microliters. Preferably, the predefined quantity of diluted blood sample is in the range of 10 to 50 microliters. For the test data obtained, the predefined quantity of diluted blood sample is in the range of 15 to 30 microliters. The diluted capillary blood mixes with the reactant mixture and the resultant mix of the diluted capillary blood and the reactant mixture is allowed to react for a predefined length of time forming a reaction solution. For ALT determination, the reaction time is in the range of 5 minutes to 60 minutes. A preferred reaction time is in the range of 10 minutes to 30 minutes. A more preferred reaction time is in the range of 20 minutes to 30 minutes. For the data obtained below, the reaction time is 25 minutes at a temperature of 40-45 degrees Celsius.

An analyte test strip 230 for measuring pyruvate in the reaction solution is used for the test. The pyruvate test strip reaction uses pyruvate oxidase in the sensor strip reagent matrix. The reaction equation is as follows:

$$\text{pyruvate} + \text{phosphate} + \text{Med}_{ox} \xrightarrow[\text{FAD, TPP, Mg}^{++}]{\text{pyruvate oxidase}} \text{acetylphosphate} + CO_2 + \text{Med}_{red}$$

$$\text{Med}_{red} - e \xrightarrow{\text{electrode}} \text{Med}_{ox}$$

where $\text{Med}_{ox}$ in the oxidized form of the mediator and $\text{Med}_{red}$ is the reduced form of the mediator.

The biasing potential across the working electrode and the reference electrode for the pyruvate sensor is in the range of 100 mv to 500 mv, preferably in the range of 300 mV to 400 mV. The voltage value in the range is not critical but it must be constant. The biasing potential across the working electrode and the reference electrode causes the mediator to change from a reduced state to an oxidized state at the electrode surface and thereby generates the current based on the concentration of pyruvate in the reaction product.

As can be seen from Eq. 1, an analyte sensor strip for measuring glutamate can also be used in place of the pyruvate sensor strip. The glutamate test strip reaction uses glutamate oxidase or glutamate dehydrogenase in the sensor strip reagent matrix. The reaction equation is as follows:

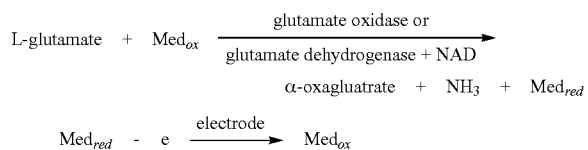

$$\text{Med}_{red} - e \xrightarrow{\text{electrode}} \text{Med}_{ox}$$

where $\text{Med}_{ox}$ in the oxidized form of the mediator and $\text{Med}_{red}$ is the reduced form of the mediator.

The biasing potential across the working electrode and the reference electrode for the glutamate sensor is in the range of 100 mv to 500 mv, preferably in the range of 300 mV to 400 mV. Like the pyruvate sensor, the voltage value in the range is not critical but it must be constant. The biasing potential across the working electrode and the reference electrode causes the mediator to change from a reduced state to an oxidized state at the electrode surface and thereby generates the current based on the concentration of glutamate in the reaction product.

The concentration values of the blood samples for ALT were obtained using a blood analyzer known as the Dimension RxL Chemistry Analyzer, which is sold by Siemens Healthcare Diagnostics, Inc. in Tarrytown, NY The test data from the analyte test strips were obtained using a CH Instruments Potentiostat, model no. CHI 812B or model no. CHI 660A.

Test Data for ALT Determination Using Pyruvate Sensor

To determine the linearity response between the blood ALT concentrations and the response based on the pyruvate test strip, the tests used 3 different concentration levels of ALT. The levels are 61 IU/L, 135 IU/L and 468 IU/L. Samples were prepared for these ALT levels and 10 current measurements were performed for each ALT concentration. For each measurement, a new pyruvate sensor strip was used. Table 1 illustrates the test data obtained for the determination of ALT.

TABLE 1

| ALT levels | Measurements (uA) | | | | | | | | | | mean | CV % |
|---|---|---|---|---|---|---|---|---|---|---|---|---|
| | 1 | 2 | 3 | 4 | 5 | 6 | 7 | 8 | 9 | 10 | | |
| 61 IU/L | 0.636 | 0.674 | 0.674 | 0.627 | 0.633 | 0.600 | 0.651 | 0.637 | 0.642 | 0.629 | 0.634 | 3.1 |
| 135 IU/L | 0.941 | 0.929 | 0.911 | 0.905 | 0.926 | 0.917 | 0.932 | 0.909 | 0.942 | 0.948 | 0.926 | 1.6 |
| 468 IU/L | 2.528 | 2.508 | 2.461 | 2.497 | 2.456 | 2.369 | 2.326 | 2.329 | 2.376 | 2.567 | 2.442 | 3.5 |

Figure 17:
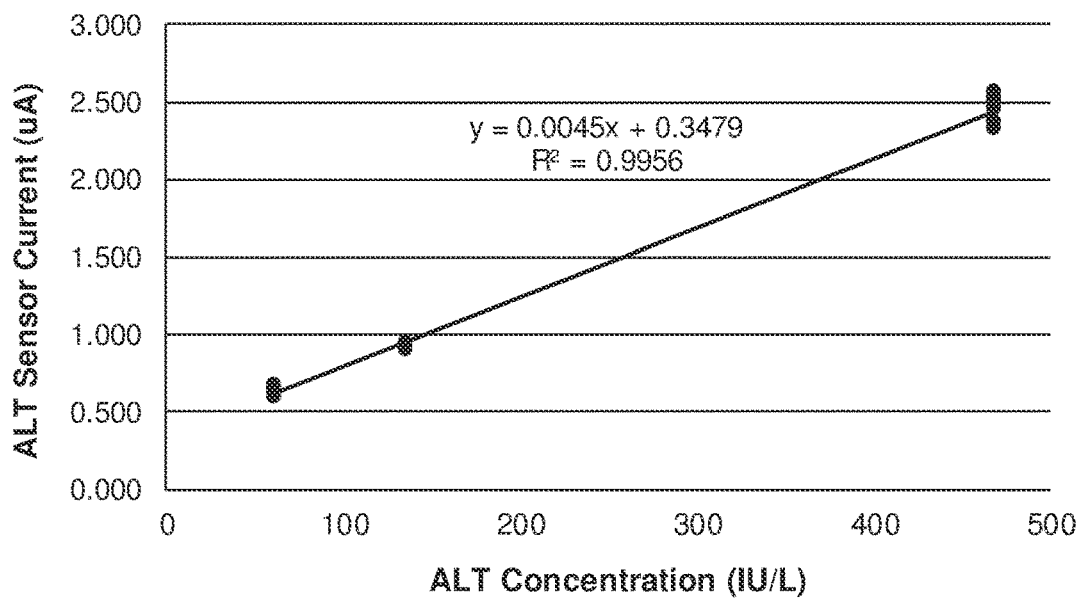
FIG. 17 is a graphic representation of the data in Table 1 showing the results for ALT sensor current versus ALT concentration using a pyruvate strip sensor.

FIG. 17 shows the measured current response of the working electrode (i.e. pyruvate oxidase-based electrode) to varying ALT concentrations. The current response is linear to the pyruvate concentration throughout the ALT concentration range tested. The ALT concentration is directly proportional to the pyruvate concentration.

Test Data for ALT Determination Using Glutamate Sensor

To determine the linearity response between the blood ALT concentrations and the response based on the glutamate test strip, the tests used 3 different concentration levels of ALT. The levels are 61 IU/L, 269 IU/L and 468 IU/L. Samples were prepared for these ALT levels and 3 current measurements were performed for each ALT concentration. For each measurement, a new glutamate sensor strip was used. Table 2 illustrates the test data obtained for the determination of ALT using the glutamate sensor strip.

TABLE 2

| ALT levels | Measurements (uA) | | | mean | CV % |
|---|---|---|---|---|---|
| | 1 | 2 | 3 | | |
| 61 IU/L | 0.402 | 0.398 | 0.396 | 0.396 | 1.3 |
| 269 IU/L | 1.024 | 1.127 | 0.965 | 1.039 | 6.45 |
| 468 IU/L | 1.658 | 1.717 | 1.599 | 1.658 | 2.91 |

Figure 18:
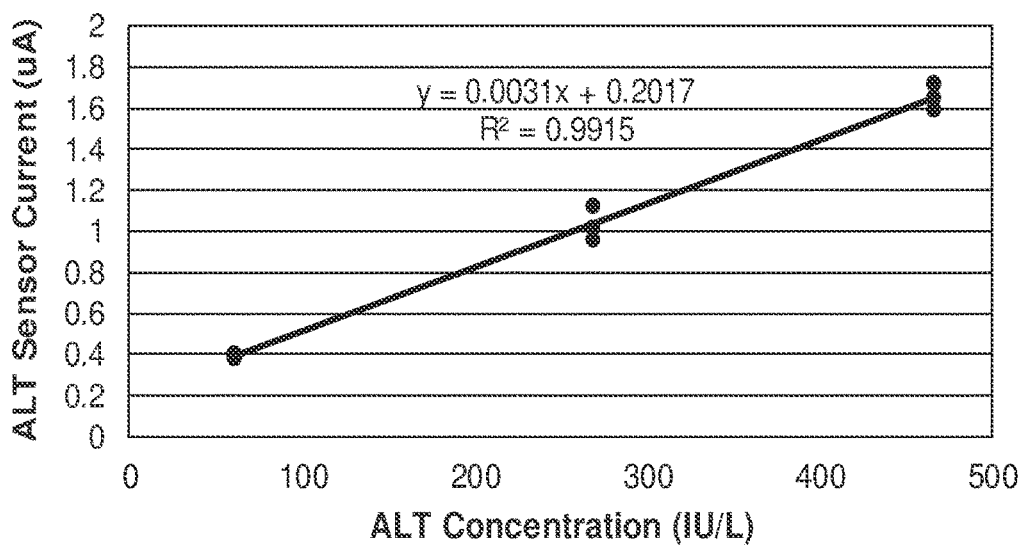
FIG. 18 is a graphic representation of the data in Table 2 showing the results for ALT sensor current versus ALT concentration using a glutamate strip sensor.

FIG. 18 shows the measured current response of the working electrode (i.e. glutamate dehydrogenase-based electrode) to varying ALT concentrations. The current response is linear to the glutamate concentration throughout the ALT concentration range tested. The ALT concentration is directly proportional to the glutamate concentration.

Determination of AST in a Blood Sample

In the presence of AST as the catalyst, L-aspartate and α-ketoglutarate undergo a reaction that produces oxalacetate and L-glutamate. This is represented by Eq. 2:

$$L - \text{aspartate} + \alpha - \text{ketoglutarate} \xrightarrow{AST} \text{oxalacetate} + L - \text{glutamate} \quad \text{Eq. 2}$$

In this situation, a glutamate sensing test strip is used for the determination of AST and is represented by the reaction previously discussed above that includes glutamate oxidase or glutamate dehydrogenase in the reagent matrix of the glutamate test strip. However, the pyruvate sensor is preferable since it is more accurate in its results. In order to use a pyruvate test strip, an additional chemical compound is required as discussed below.

The oxaloacetate product from Eq. 2 can also undergo a further reaction in the presence of oxaloacetate decarboxylase that produces pyruvate and carbon dioxide. This is represented by Equation 3:

oxaloacetate+oxaloacetate decarboxylase→pyruvate+ $CO_2$   Eq. 3

Hence, if oxaloacetate decarboxylase is in the reactant mixture in the cartridge chamber 22, pyruvate is formed and a pyruvate test strip may be used to measure the pyruvate present in the reaction solution. The concentration of AST in the blood sample is directly proportional to the concentration of pyruvate measured.

After dilution, a predefined quantity of the diluted blood sample is pipetted into the chamber 22 of the disposable test cartridge 10 that contains the reactant mixture for determining the AST activity in the blood sample. The amount of the predefined quantity of diluted blood sample is in the range of 5 to 100 microliters. Preferably, the predefined quantity of diluted blood sample is in the range of 10 to 50 microliters.

For the test data obtained, the predefined quantity of diluted blood sample is in the range of 15 to 30 microliters. The diluted capillary blood mixes with the reactant mixture and the resultant mix of the diluted capillary blood and the reactant mixture is allowed to react for a predefined length of time forming a reaction solution. For AST determination, the reaction time is in the range of 5 minutes to 60 minutes. A preferred reaction time is in the range of 10 minutes to 30 minutes. A more preferred reaction time is in the range of 20 minutes to 30 minutes. For the data obtained below, the reaction time is 25 minutes at a temperature of 40-45 degrees Celsius.

As previously discussed for measuring AST, an analyte test strip 230 for measuring pyruvate in the reaction solution is used for the test when oxaloacetate decarboxylase is present in the reactant mixture of the disposable test cartridge 10. The pyruvate test strip reaction uses pyruvate oxidase in the sensor strip reagent matrix. The reaction equation is as previously discussed above for the pyruvate test strip.

As previously disclosed for the ALT determination, the concentration values of the blood samples for AST were obtained using a blood analyzer known as the Dimension R×L Chemistry Analyzer, which is sold by Siemens Healthcare Diagnostics, Inc. in Tarrytown, NY The test data from the analyte test strips were obtained using a CH Instruments Potentiostat, model no. CHI 812B or model no. CHI 660A.

Test Data for AST Determination Using Pyruvate Sensor

To determine the linearity response between the blood AST concentrations and the response based on the pyruvate test strip, the tests used 3 different concentration levels of AST. The levels are 25 IU/L, 196 IU/L and 698 IU/L. Samples were prepared for these AST levels and 10 current measurements were performed for each AST concentration. For each measurement, a new pyruvate sensor strip was used. Table 3 illustrates the test data obtained for the determination of AST.

duces phenol or its derivatives and phosphate. This is represented by Equation 4:

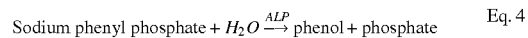

$$\text{Sodium phenyl phosphate} + H_2O \xrightarrow{ALP} \text{phenol} + \text{phosphate} \quad \text{Eq. 4}$$

As previously explained for the ALT and AST determinations, after dilution, a predefined quantity of the diluted blood sample is pipetted into the chamber 22 of the disposable test cartridge 10 that contains the reactant mixture for determining the ALP activity in the blood sample. The amount of the predefined quantity of diluted blood sample is in the range of 5 to 100 microliters. Preferably, the predefined quantity of diluted blood sample is in the range of 10 to 50 microliters. For the test data obtained, the predefined quantity of diluted blood sample is in the range of 15 to 30 microliters. The diluted capillary blood mixes with the reaction mixture and resultant mix of the diluted capillary blood and the reaction mixture is allowed to react for a predefined length of time. For ALP determination, the reaction time is in the range of 5 minutes to 60 minutes. A preferred reaction time is in the range of 10 minutes to 30 minutes. A more preferred reaction time is in the range of 20 minutes to 30 minutes. For the data obtained below, the reaction time is 25 minutes at a temperature of 40-45 degrees Celsius.

Unlike the sensor strips used in the ALT and AST determination, no enzyme or mediator are required in the reagent matrix for the working electrode. This is because the reactant product phenol seen in Eq. 4 above is electrochemically oxidized directly at the electrode surface.

The concentration values of the blood samples for ALP were obtained using a blood analyzer known as the Dimension R×L Chemistry Analyzer, which is sold by Siemens Healthcare Diagnostics, Inc. in Tarrytown, NY The test data from the analyte test strips were obtained using a CH Instruments Potentiostat, model no. 812B or model no. 660A.

TABLE 3

| AST levels | Measurements (uA) | | | | | | | | | | | |
|---|---|---|---|---|---|---|---|---|---|---|---|---|
| | 1 | 2 | 3 | 4 | 5 | 6 | 7 | 8 | 9 | 10 | mean | CV % |
| 25 IU/L | 0.355 | 0.417 | 0.432 | 0.449 | 0.358 | 0.396 | 0.399 | 0.381 | 0.387 | 0.399 | 0.397 | 7.1 |
| 196 IU/L | 1.024 | 1.172 | 1.148 | 1.166 | 1.118 | 1.012 | 1.118 | 1.083 | 1.062 | 1.047 | 1.095 | 5.0 |
| 698 IU/L | 3.936 | 4.084 | 4.046 | 4.025 | 3.791 | 3.981 | 4.075 | 4.084 | 3.735 | 3.797 | 3.955 | 3.2 |

Figure 19:
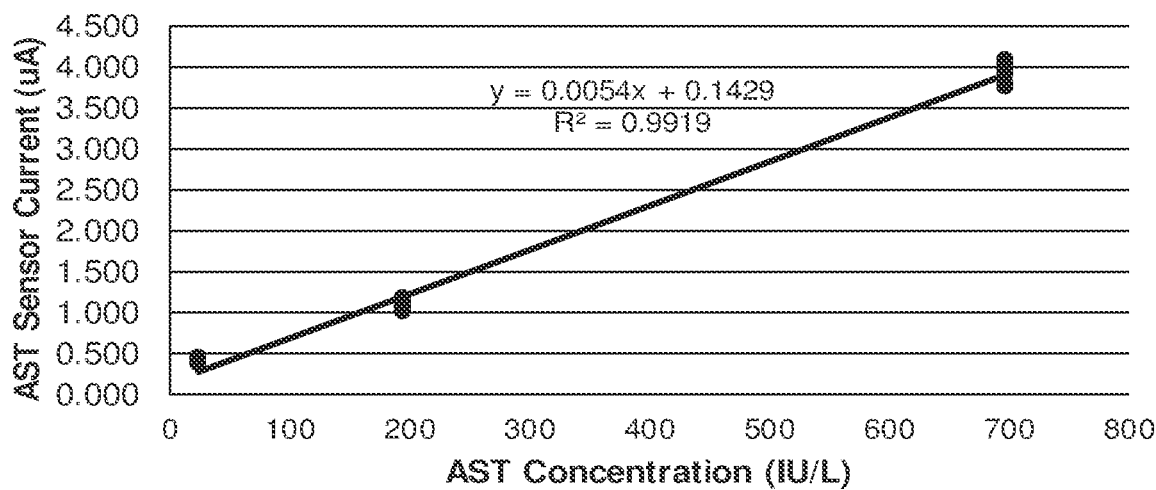
FIG. 19 is a graphic representation of the data in Table 3 showing the results for AST sensor current versus AST concentration using a pyruvate sensor.

FIG. 19 shows the measured current response of the working electrode (i.e. pyruvate oxidase-based electrode) to varying AST concentrations. The current response is linear to the pyruvate concentration throughout the AST concentration range tested. The AST concentration is directly proportional to the pyruvate concentration (or glutamate when glutamate oxidase or glutamate dehydrogenase is used).

Determination of ALP in a Blood Sample

In the presence of ALP as the catalyst, sodium phenyl phosphate or its derivatives undergoes a reaction that pro- Test Data for ALP Determination Using Current Sensor To determine the linearity response between the blood ALP concentrations and the response based on current-measuring test strip, the tests used 3 different concentration levels of ALP. The levels are 72 IU/L, 178 IU/L and 458 IU/L. Samples were prepared for these ALP levels and 10 current measurements were performed for each ALP concentration. For each measurement, a new current sensor strip was used. Table 4 illustrates the test data obtained for the determination of ALP.

TABLE 4

| ALP levels | Measurements (uA) | | | | | | | | | | mean | CV % |
|---|---|---|---|---|---|---|---|---|---|---|---|---|
| | 1 | 2 | 3 | 4 | 5 | 6 | 7 | 8 | 9 | 10 | | |
| 72 IU/L | 2.165 | 2.231 | 2.154 | 2.085 | 2.136 | 2.205 | 2.114 | 2.305 | 2.196 | 2.258 | 2.185 | 3.1 |
| 178 IU/L | 2.801 | 2.744 | 2.716 | 2.697 | 2.735 | 2.789 | 2.758 | 2.687 | 2.812 | 2.749 | 2.749 | 1.5 |
| 458 IU/L | 3.659 | 3.706 | 3.784 | 3.658 | 3.765 | 3.639 | 3.801 | 3.754 | 3.699 | 3.719 | 3.718 | 1.5 |

Figure 20:
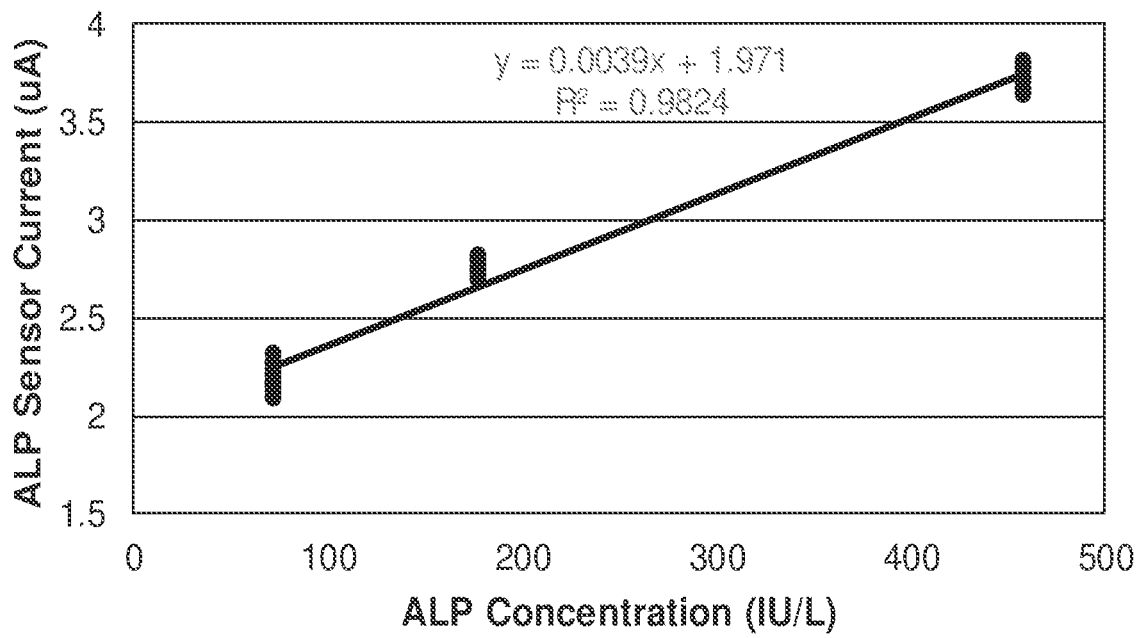
FIG. 20 is a graphic representation of the data in Table 4 showing the results for ALP sensor current versus ALP concentration using a current sensor.

FIG. 20 shows the measured current response of the working electrode (i.e. current sensing electrode) to varying ALP concentrations. The current response is linear to the phenol concentration throughout the ALP concentration range tested. The ALP concentration is directly proportional to the phenol concentration.

Figure 21:
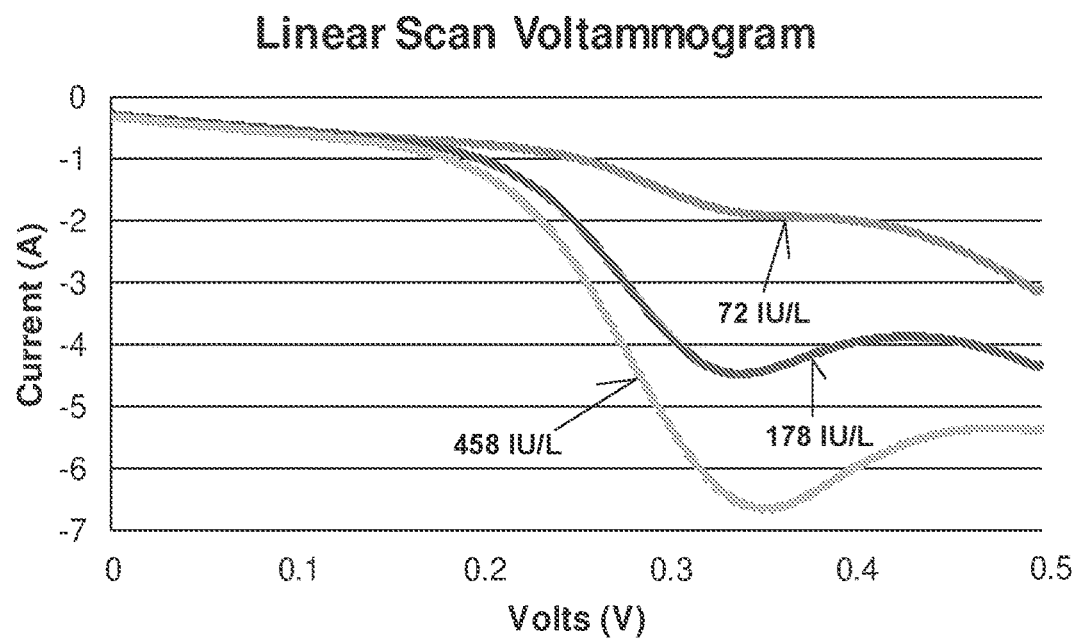

FIG. 21 is a linear scan voltammogram of the current sensor showing the current traces for the three ALP concentration standards above. The linear scan voltammogram shows that the potential scan is from 0 mV to 500 mV between the working electrode and the reference electrode. This is a non-fixed potential sensor technique. For all current tests using linear scan voltammogram, the analyte sensor strip 230, 430 undergoes a current scan between 0 mV and 500 mV. The current reading when using this technique is obtained when the scan gets to 350 mV due to the largest current separation between the concentration levels of ALP.

Figure 22:
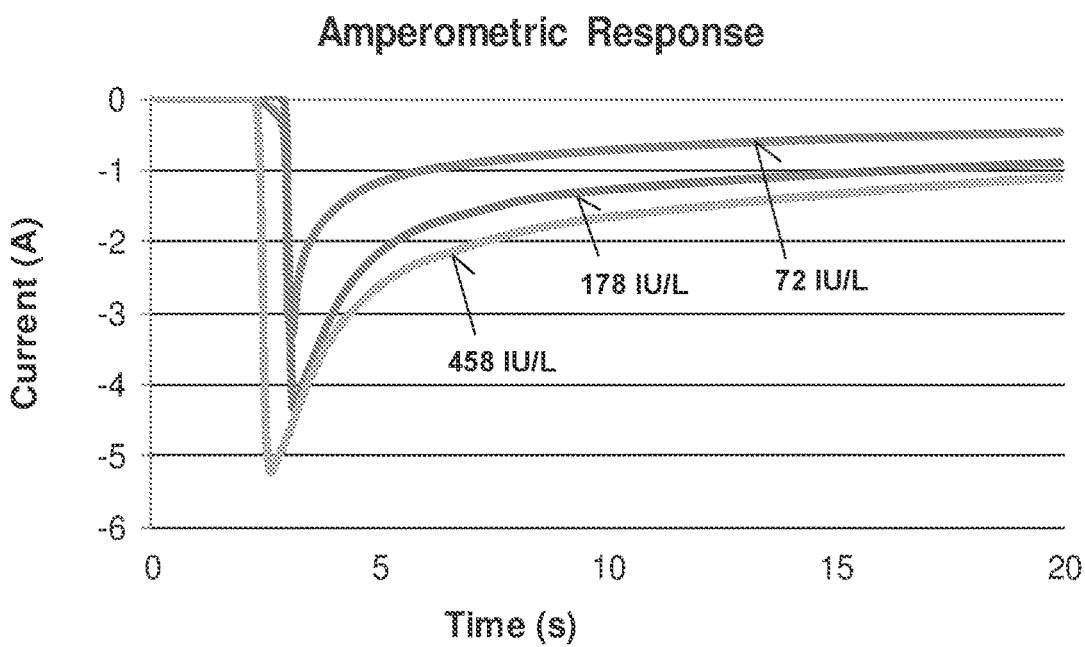
FIG. 22 is a graphic representation of the amperometric response for ALP sensor current versus time using the current sensor of FIG. 20.

FIG. 22 is the amperometric response plot of current versus time for the three concentrations of ALP. This amperometric technique uses a fixed potential (i.e. biasing potential) between the working electrode and the reference electrode. The fixed potential is similar to the potential for measuring ALT or AST disclosed above. This plot is used to determine when to record the current measurement after sample introduction to the current sensor strip. For all current tests using the amperometric technique for the determination of ALP, the current measurement is recorded ten seconds (i.e. the "time period") after the sample covers both the working electrode and the reference electrode. When the sample covers both the working electrode and the reference electrode, there is a large change in the current measurement. This marks the beginning of the 10 second time period. In the plot, the ten-second start time begins at the instant there is a large current change. As seen in FIG. 22, this appears at about time 2.5-3 seconds. This means that the current recording time according to the plot would be about 12.5-13 seconds. From a practical viewpoint, a timer would begin when there is a large current change sensed by the instrument and a current recording would be registered ten seconds after the start of the timer.

Determination of GGT in a Blood Sample

In the presence of GGT as the catalyst, L-glutamic acid gamma-anilide and glycylglycine undergo a reaction that produces L-gamma-glutamyl-glycylglycine and aniline. This is represented by Equation 5:

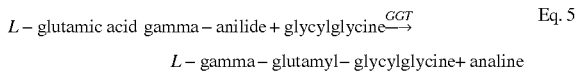

$$L-\text{glutamic acid gamma}-\text{anilide} + \text{glycylglycine} \xrightarrow{GGT} L-\text{gamma}-\text{glutamyl}-\text{glycylglycine} + \text{analine} \quad \text{Eq. 5}$$

After dilution, as explained above for the determination of ALP, a predefined quantity of the diluted blood sample is pipetted into the chamber 22 of the disposable test cartridge 10 that contains the reactant mixture for determining the GGT activity in the blood sample. The amount of the predefined quantity of diluted blood sample is in the range of 5 to 100 microliters. Preferably, the predefined quantity of diluted blood sample is in the range of 10 to 50 microliters. For the test data obtained, the predefined quantity of diluted blood sample is in the range of 15 to 30 microliters. The diluted capillary blood mixes with the reaction mixture and resultant mix of the diluted capillary blood and the reaction mixture is allowed to react for a predefined length of time. For GGT determination, the reaction time is in the range of 5 minutes to 60 minutes. A preferred reaction time is in the range of 10 minutes to 30 minutes. A more preferred reaction time is in the range of 20 minutes to 30 minutes. For the data obtained below, the reaction time is 25 minutes at a temperature of 40-45 degrees Celsius.

Like the sensor strip for the determination of ALP, no enzyme or mediator is required in the reagent matrix for the working electrode. This is because the reactant product analine seen in Eq. 5 above is electrochemically oxidized directly at the electrode surface.

The concentration values of the blood samples for ALP were obtained using a blood analyzer known as the Dimension RxL Chemistry Analyzer, which is sold by Siemens Healthcare Diagnostics, Inc. in Tarrytown, NY The test data from the analyte test strips were obtained using a CH Instruments Potentiostat, model no. 812B or model no. 660A.

Test Data for GGT Determination Using Current Sensor

To determine the linearity response between the blood GGT concentrations and the response based on a current-measuring test strip, the tests used 3 different concentration levels of GGT. The levels are 52 IU/L, 153 IU/L and 430 IU/L. Samples were prepared for these GGT levels and 10 current measurements were performed for each GGT concentration. For each measurement, a new current-measuring test strip was used. Table 5 illustrates the test data obtained for the determination of ALP.

TABLE 5

| GGT levels | Measurements (uA) | | | | | | | | | | mean | CV % |
|---|---|---|---|---|---|---|---|---|---|---|---|---|
| | 1 | 2 | 3 | 4 | 5 | 6 | 7 | 8 | 9 | 10 | | |
| 52 IU/L | 2.217 | 2.113 | 2.096 | 2.223 | 2.156 | 2.193 | 2.208 | 2.194 | 2.231 | 2.204 | 2.184 | 2.1 |
| 153 IU/L | 2.912 | 2.885 | 2.906 | 2.944 | 2.817 | 2.883 | 2.906 | 2.795 | 2.809 | 2.935 | 2.879 | 1.9 |
| 430 IU/L | 4.562 | 4.497 | 4.625 | 4.608 | 4.577 | 4.637 | 4.551 | 4.483 | 4.623 | 4.522 | 4.569 | 1.2 |

Figure 23:
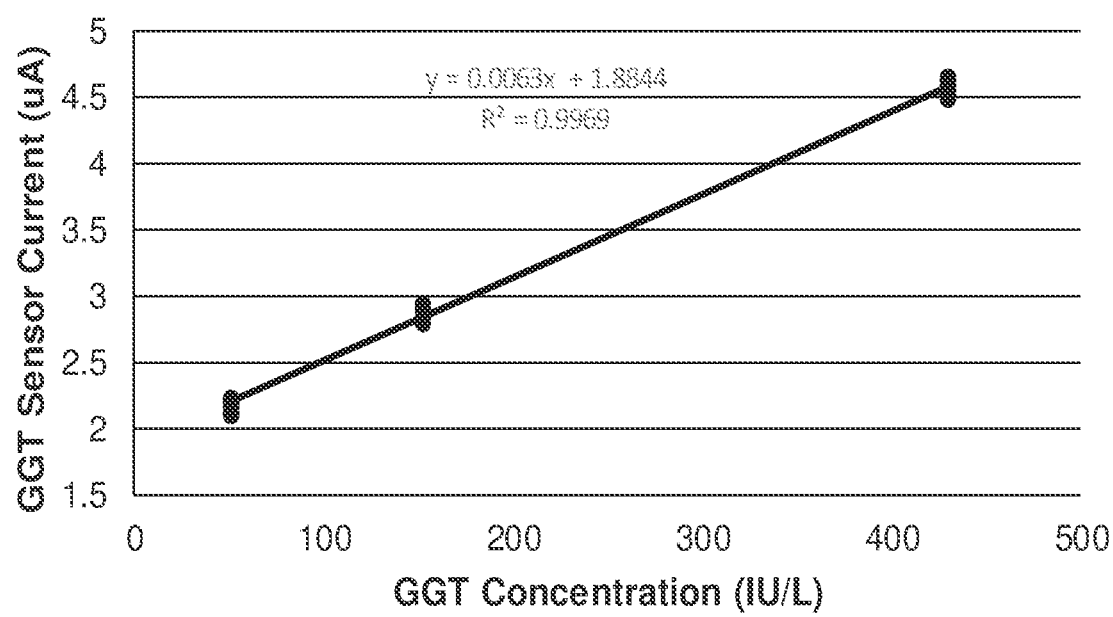
FIG. 23 is a graphic representation of the data in Table 5 showing the results for GGT sensor current versus GGT concentration using a current sensor.

FIG. 23 shows the measured current response of the working electrode (i.e. current sensing electrode) to varying GGT concentrations. The current response is linear to the aniline concentration throughout the GGT concentration range tested. The GGT concentration is directly proportional to the aniline concentration.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable test cartridge for use in a point-of-care analyzer to determine the concentration of one or more liver enzymes in a blood sample, the disposable test cartridge comprising:
    a cartridge body having a plurality of chambers wherein each of the plurality of chambers has an opening at a top of the cartridge body and at least one of the plurality of chambers contains a reactant mixture capable of undergoing a chemical reaction when combined with a blood sample forming a reaction solution containing at least one reaction product, the reactant mixture containing chemicals specific for being catalyzed by one of the liver enzymes alanine aminotransferase (ALT), aspartate aminotransferase (AST), alkaline phosphatase (ALP), or gamma-glutamyl transferase (GGT) in the blood sample;
    a removable cartridge cover connected to the cartridge body and covering the plurality of chambers, the removable cartridge cover having a capillary-receiving aperture and a capillary element removably insertable into the cartridge cover, the capillary element configured for obtaining a blood sample; and
    a test strip module directly connected to the cartridge body and containing at least one analyte test strip configured for receiving a portion of the reaction solution and measuring at least one analyte, the at least one analyte being the at least one reaction product.

2. The disposable test cartridge of claim 1 wherein the reactant mixture containing chemicals specific to the determination of ALT includes L-alanine and α-ketoglutarate.

3. The disposable test cartridge of claim 1 wherein the reactant mixture containing chemicals specific to the determination of AST includes L-aspartate and α-ketoglutarate.

4. The disposable test cartridge of claim 1 wherein the reactant mixture containing chemicals specific to the determination of AST includes L-aspartate, α-ketoglutarate and oxaloacetate decarboxylase.

5. The disposable test cartridge of claim 1 wherein the reactant mixture containing chemicals specific to the determination of ALP includes sodium phenyl phosphate or its derivatives.

6. The disposable test cartridge of claim 1 wherein the reactant mixture containing chemicals specific to the determination of GGT includes L-glutamic acid gamma-anilide or its derivatives and glycylglycine.

7. The disposable test cartridge of claim 1 wherein the test strip module incorporates an analyte test strip configured for measuring pyruvate or L-glutamate when the at least one of the plurality of chambers contains chemicals specific for being catalyzed by one of the liver enzymes ALT or AST.

8. The disposable test cartridge of claim 1 wherein the test strip module incorporates an analyte test strip configured for measuring phenol when the at least one of the plurality of chambers contains chemicals that are catalyzed by the liver enzyme ALP.

9. The disposable test cartridge of claim 1 wherein the test strip module incorporates an analyte test strip configured for measuring aniline when the at least one of the plurality of chambers contains chemicals that are catalyzed by the liver enzyme GGT.

10. The disposable test cartridge of claim 1 wherein the test strip module incorporates an analyte test strip having a reagent matrix disposed on a working electrode containing one of pyruvate oxidase, glutamate oxidase or glutamate dehydrogenase.

11. The disposable test cartridge of claim 1 wherein the test strip module incorporates an analyte test strip having a reagent matrix disposed on a working electrode wherein the reagent matrix does not contain an enzyme or a mediator.

12. The disposable test cartridge of claim 1 wherein the analyte test strip has an electrical contact end, a sample end and a sample receiving port spaced a predefined distance from the sample end.

13. The disposable test cartridge of claim 12 wherein the sample end includes a vent opening and a sample channel between the sample receiving port and the vent opening.

14. The disposable cartridge of claim 1 wherein the test strip module incorporates two or more analyte test strips wherein at least two of the two or more analyte test strips measures the same analyte.

15. The disposable cartridge of claim 1 wherein the test strip module incorporates two or more analyte test strips wherein each of the two or more analyte test strips measures different analytes.

16. The disposable test cartridge of claim 1 wherein the removable cartridge cover covers a top surface of the cartridge body and the test strip module is connected to a side surface of the cartridge body, whereby the at least one analyte test strip is laterally spaced from the cartridge cover capillary-receiving aperture.

17. A method of determining the concentration of one or more liver enzymes in a blood sample, the method comprising:
    providing the disposable test cartridge of claim 1, wherein the plurality of chambers comprises a reactant chamber containing predefined chemicals that are catalyzed by one of the liver enzymes ALT, AST, ALP, or GGT in the blood sample, and wherein the disposable test cartridge further comprises a blood sample receiving chamber;

obtaining the blood sample and placing at least a portion of the blood sample in the sample receiving chamber;

diluting the blood sample forming a diluted blood sample;

disposing a predefined amount of the diluted blood sample into the reactant chamber;

allowing a reaction between the predefined chemicals and the diluted blood sample to continue for a predefined time period forming a reaction solution containing at least one reaction product;

transferring a portion of the reaction solution to the analyte test strip capable of measuring an amount of the at least one reaction product in the reaction solution;

measuring the amount of the at least one reaction product present in the reaction solution; and correlating the amount of the at least one reaction product in the reaction solution to the amount of one of the liver enzymes ALT, AST, ALP, or GGT in the blood sample.

18. The method of claim 17 wherein the measuring step further includes measuring an amount of one of pyruvate, glutamate, phenol, or aniline in the reaction solution.

19. The method of claim 18 wherein the correlating step further includes correlating the amount of one of pyruvate, glutamate, phenol, or aniline in the reaction solution to the amount, respectively, of ALT, AST, ALP, or GGT in the blood sample.

20. The method of claim 17, the measuring step comprising an electrochemical measurement technique to measure the at least one reaction product.

21. The method of claim 17, the measuring step comprising amperometry to measure the at least one reaction product for the determination of ALT, AST, ALP, or GGT.

22. The method of claim 17, the measuring step comprising linear sweep voltammetry to measure the at least one reaction product for the determination of ALP.

23. A disposable cartridge kit for use in a point-of-care analyzer to determine the concentration of one or more liver enzymes in a blood sample, the disposable cartridge kit comprising:

a disposable test cartridge comprising:
  a cartridge body having a plurality of chambers wherein each of the plurality of chambers has an opening at a top of the cartridge body and at least one of the plurality of chambers contains a reactant mixture capable of undergoing a chemical reaction when combined with a blood sample forming a reaction solution containing at least one reaction product, the reactant mixture containing chemicals specific for being catalyzed by one of the liver enzymes ALT, AST, ALP, or GGT in the blood sample;
  a removable cartridge cover connected to the cartridge body and covering the plurality of chambers, the removable cartridge cover having a capillary-receiving aperture and a removable capillary element removably insertable into the cartridge cover, the capillary element configured for obtaining a blood sample;
  a disposable pipette tip disposed in one of the plurality of chambers; and
  a test strip module directly connected to the cartridge body and containing at least one analyte test strip configured for receiving a portion of the reaction solution and measuring at least one analyte, the at least one analyte being the at least one reaction product.

24. The kit of claim 23 further comprising instructions on the use of the disposable test cartridge and use of the capillary element.

25. The kit of claim 23 wherein the removable cartridge cover covers a top surface of the cartridge body and the test strip module is connected to a side surface of the cartridge body, whereby the at least one analyte test strip is laterally spaced from the cartridge cover capillary-receiving aperture.

26. A method of electrochemically determining the concentration of one or more liver enzymes in a blood sample using a point-of-care analyzer, the method comprising:

providing a point-of-care analyzer;

obtaining a disposable test cartridge for use in the point-of-care analyzer, the disposable test cartridge comprising:
  a cartridge body having a plurality of chambers wherein each of the plurality of chambers has an opening at a top of the cartridge body and at least one of the plurality of chambers contains a
  reactant mixture capable of undergoing a chemical reaction when combined with a blood sample forming a reaction solution containing at least one reaction product, the reactant mixture containing chemicals specific for being catalyzed by one of the liver enzymes ALT, AST, ALP, or GGT in the blood sample;
  a removable cartridge cover connected to the cartridge body and covering the plurality of chambers, the removable cartridge cover having a capillary-receiving aperture and a removable capillary element removably insertable into the cartridge cover, the capillary element configured for obtaining a blood sample;
  a disposable pipette tip disposed in one of the plurality of chambers; and
  a test strip module directly connected to the cartridge body and containing at least one analyte test strip configured for receiving a portion of the reaction solution and measuring at least one analyte, the at least one analyte being the at least one reaction product;

removing the capillary element from the removable cartridge cover, receiving a blood sample in the capillary element and replacing the capillary element containing the blood sample into the removable cartridge cover;

placing the disposable test cartridge into the point-of-care analyzer; and initiating a test cycle in the point-of-care analyzer.

27. The method of claim 26 wherein the initiating step further includes:

aspirating the blood sample from the capillary element into a bottom of a chamber directly below the capillary element; removing the cartridge cover from the cartridge body;

attaching the pipette tip to an automated pipettor device within the point-of-care analyzer;

diluting the blood sample by pipetting a predefined amount of a diluent from another of the plurality of chambers and depositing the predefined amount into the chamber containing the blood sample forming a diluted blood sample;

removing a predefined amount of the diluted blood sample and depositing the predefined amount of the diluted blood sample by pipetting the predefined amount into another of the plurality of chambers containing the reactant mixture of chemicals specific for being catalyzed by one of the liver enzymes ALT, AST, ALP, or GGT in the blood sample forming a reaction solution;

after a predefined reaction time, removing a predefined amount of the reaction solution and depositing onto the at least one analyte test strip to measure the at least one analyte;

measuring the amount of the at least one analyte in the reaction solution; and correlating the amount of the at least one analyte in the reaction solution to the amount of one of the liver enzymes ALT, AST, ALP, or GGT in the blood sample.

28. The method of claim 26 wherein the measuring step includes measuring the amount of one of pyruvate, glutamate, phenol, or aniline in the reaction solution.

29. The method of claim 28, the measuring step comprising amperometry to measure the at least one reaction product for the determination of ALT, AST, ALP, or GGT.

30. The method of claim 28, the measuring step comprising linear sweep voltammetry to measure the at least one reaction product for the determination of ALP.

31. The method of claim 26 wherein the removable cartridge cover covers a top surface of the cartridge body and the test strip module is connected to a side surface of the cartridge body, whereby the at least one analyte test strip is laterally spaced from the cartridge cover capillary-receiving aperture.

\* \* \* \* \*